US011478475B2

(12) United States Patent
Indraccolo et al.

(10) Patent No.: US 11,478,475 B2
(45) Date of Patent: Oct. 25, 2022

(54) INHIBITOR OF HISTONE DEACETYLASE 6 IN THE TREATMENT OF T-CELL ACUTE LYMPHOBLASTIC LEUKEMIA (T-ALL) AND OTHER NEOPLASIA WITH HIGH EXPRESSION OF NOTCH-3

(71) Applicant: ISTITUTO ONCOLOGICO VENETO IOV-IRCCS, Padua (IT)

(72) Inventors: Stefano Indraccolo, Padua (IT); Marica Pinazza, Padua (IT)

(73) Assignee: ISTITUTO ONCOLOGICO VENETO IOV-IRCCS

( * ) Notice: Subject to any disclaimer, the term of this patent is extended or adjusted under 35 U.S.C. 154(b) by 153 days.

(21) Appl. No.: 16/632,956

(22) PCT Filed: Jul. 26, 2018

(86) PCT No.: PCT/IB2018/055605
§ 371 (c)(1),
(2) Date: Jan. 22, 2020

(87) PCT Pub. No.: WO2019/021239
PCT Pub. Date: Jan. 31, 2019

(65) Prior Publication Data
US 2020/0155549 A1    May 21, 2020

(30) Foreign Application Priority Data
Jul. 27, 2017  (IT) .......................... 102017000086293

(51) Int. Cl.
| A61K 31/505 | (2006.01) |
| A61P 35/00 | (2006.01) |
| A61K 9/00 | (2006.01) |
| A61K 31/573 | (2006.01) |
| A61K 31/69 | (2006.01) |

(52) U.S. Cl.
CPC .......... *A61K 31/505* (2013.01); *A61K 9/0053* (2013.01); *A61K 31/573* (2013.01); *A61K 31/69* (2013.01); *A61P 35/00* (2018.01)

(58) Field of Classification Search
None
See application file for complete search history.

(56) References Cited

PUBLICATIONS

Chadwick et al., Blood Cells, Molecues & Diseases (2010), 45(3), pp. 201-209.*
International Search Report, issued in PCT/IB2018/055605, dated Oct. 24, 2018, Rijswijk, Netherlands.
Grace I. Aldana-Masangkay et al., Tubacin suppresses proliferation and induces apoptosis of acute lymphoblastic leukemia cells, Leukemia and Lymphoma, Jun. 23, 2011, pp. 1544-1555, vol. 52, Issue 8, Informa, London, GB.
Rodriguez-Gonzalez Augustin et al., Targeting histone deacetylase 6 and the aggresome pathway in acute lymphoblastic leukemia cells, Blood, Nov. 16, 2007, p. 478A, vol. 110, No. 11, 49th Annual Meeting of The American Society of Hematology, Atlanta, GA, USA, Database Biosis (Online) Biosciences Information Service, Philadelphia, PA, US, Database accession No. PREV200800216874, XP002779862.
Yee Andrew J. et al, Ricolinostat plus lenalidomide, and dexamethasone in relapsed or refractory multiple myeloma: a multicentre phase 1b trial, The Lancet Oncology, Sep. 17, 2016, pp. 1569-1578, vol. 17, No. 11, Elsevier, Amsterdam, NL.
Cosenza Maria et al., Ricolinostat, a selective HDAC6 inhibitor, shows anti-lymphoma cell activity alone and in combination with bendamustine, Apoptosis, Mar. 17, 2017, pp. 827-840, vol. 22, No. 6, Springer, London, GB.
Michela Colombo et al., Notch signaling deregulation in multiple myeloma: A rational molecular target, Oncotarget, Sep. 29, 2015, pp. 26826-26840, vol. 6, No. 29, Impact Journals, LLC.
Batchu S. N. et al., The therapeutic hope for HDAC6 inhibitors in malignancy and chronic disease, Clinical Science, May 6, 2016, pp. 987-1003, vol. 130, Issue 12, Portland Press Limited on behalf of the Biochemical Society, London, GB.
Preeti Putcha,HDAC6 as a Therapeutic Candidate in the Treatment of Inflammatory Breast Cancers, Dec. 31, 2015, pages i-98, Columbia University, Retrieved from the Internet: https://academiccommons.columbia.edu/doi/10.7916/D83B66R1/download.
Graux C., Cools J., Michaux L., Vandenberghe P., Hagemeijer A., Cytogenetics and molecular genetics of T-cell acute lymphoblastic leukemia: from thymocyte to lymphoblast, Leukemia, Jul. 6, 2006, pp. 1496-1510, vol. 20, No. 9, Nature Publishing Group.
Weng A.P., Ferrando A.A., Lee W., Morris J.P.IV, Silverman L.B., Sanchez-Irizarry C. et al., Activating mutations of NOTCH1 in human T cell acute lymphoblastic leukemia, Science, Oct. 8, 2004, pp. 269-271, vol. 306, Issue 5694, AAAS, USA.
Bellavia D., Campese A.F., Alesse E., Vacca A., Felli M.P., Balestri A. et al., Constitutive activation of NF-kappaB and T-cell leukemia/lymphoma in Notch3 transgenic mice, The Embo Journal, Jul. 3, 2000, pp. 3337-3348, vol. 19, Issue 13, Embo Press, DE.
Bellavia D., Campese A.F., Vacca A., Gulino A., Screpanti I., Notch3, another Notch in T cell development, Seminars in Immunology, Apr. 2003, pp. 107-112, vol. 15, Issue 2, Elsevier.
Fortini Mark E., Notch signaling: The Core Pathway and its Posttranslational Regulation, Developmental Cell, May 19, 2009, pp. 633-647, vol. 16, Issue 5, Cell Press, Elsevier Inc.
Seugnet L., Simpson P., Haenlin M., Requirement for Dynamin during Notch Signaling in *Drosophila* Neurogenesis, Developmental Biology, Dec. 15, 1997, pp. 585-598, vol. 192, Issue 2, Elsevier Inc.
Lu H., Bilder D., Endocytic control of epithelial polarity and proliferation in *Drosophila*, Nature Cell Biology, Oct. 30, 2005, pp. 1232-1239, vol. 7, Issue 12, Nature Publishing Group.
Kanwar R., Fortini M. E., Notch Signaling: A Different Sort Makes the Cut, Current Biology, Dec. 29, 2004, R1043-1045, vol. 14, Issue 24, Elsevier Ltd.
Weber U., Eroglu C., Mlodzik M., Phospholipid Membrane Composition Affects EGF Receptor and Notch Signaling through Effects on Endocytosis during *Drosophila* Development, Developmental Cell, Oct. 2003, pp. 559-570, vol. 5, Issue 4, Cell Press.

(Continued)

*Primary Examiner* — Brian J Davis
(74) *Attorney, Agent, or Firm* — Valauskas Corder LLC

(57) ABSTRACT

A method for treating T-cell acute lymphoblastic leukemia (T-ALL) and other neoplasia with high expression of Notch3 is provided.

20 Claims, 24 Drawing Sheets

(56) References Cited

PUBLICATIONS

Liu J., Shen JX., Wen XF., Guo YX., Zhang GJ., Targeting Notch degradation system provides promise for breast cancer therapeutics, Critical Reviews in Oncology/Hematology, Aug. 2016, pp. 21-29, vol. 104, Elsevier.

Bolden J.E., Peart M.J., Johnstone R.W., Anticancer activities of histone deacetylase inhibitors, Nature Review Drug Discovery, Sep. 1, 2006, pp. 769-784, vol. 5, Issue 9, Springer.

Aldana-Masangkay G.I., Sakamoto K.M., The Role of HDAC6 in Cancer, Journal of Biomedicine and Biotechnology, Nov. 7, 2010, pp. 1-10, vol. 2011, Article ID 875824, Hindawi Publishing Corporation, London, GB.

Deribe Y.L., Wild P., Chandrashaker A., Curak J., Schmidt M.H., Kalaidzidis Y., et al., Regulation of Epidermal Growth Factor Receptor Trafficking by Lysine Deacetylase HDAC6, Science Signalling, Dec. 22, 2009, pp. ra84, vol. 2, Issue 102, AAAS.

Gao YS., Hubbert C.C., Yao TP., The Microtubule-associated Histone Deacetylase 6 (HDAC6) Regulates Epidermal Growth Factor Receptor (EGFR) Endocytic Trafficking and Degradation, The Journal of Biological Chemistry, Apr. 9, 2010, pp. 11219-11226, vol. 285, No. 15, The American Society for Biochemistry and Molecular Biology, Inc., USA.

Ali S.R., Humphreys K.J., Mckinnon R.A., Michael M.Z., Impact of Histone Deacetylase Inhibitors on microRNA Expression and Cancer Therapy: A Review, Drug Development Research, Aug. 25, 2015, pp. 296-317, vol. 76, Issue 6, Wiley.

San-Miguel JF, Hungria VT, Yoon SS, Beksac M, Dimopoulos MA, Elghandour A. et al., Panobinostat plus bortezomib and dexamethasone versus placebo plus bortezomib and dexamethasone in patients with relapsed or relapsed and refractory multiple myeloma: a multicentre, randomised, double-blind phase 3 trial, The Lancet Oncology, Oct. 1, 2014, pp. 1195-1206, vol. 15, Issue 11, Elsevier.

Gu Y., Masiero M., Banham A.H., Notch signaling: its roles and therapeutic potential in hematological malignancies, Oncotarget, May 17, 2016, pp. 29804-29823, vol. 7, No. 20, Impact Journals, LLC.

Brian Deskin et al., Requirement of HDAC6 for activation of Notch1 by TGF-β1, Scientific Reports, Aug. 8, 2016, pp. 1-9, vol. 6, No. 1, Springer.

* cited by examiner

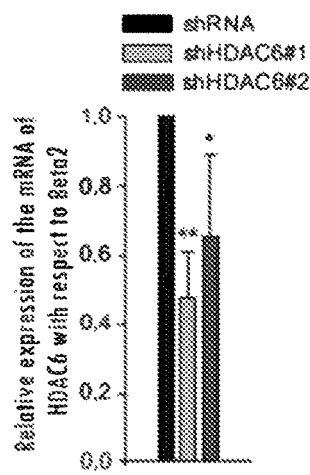 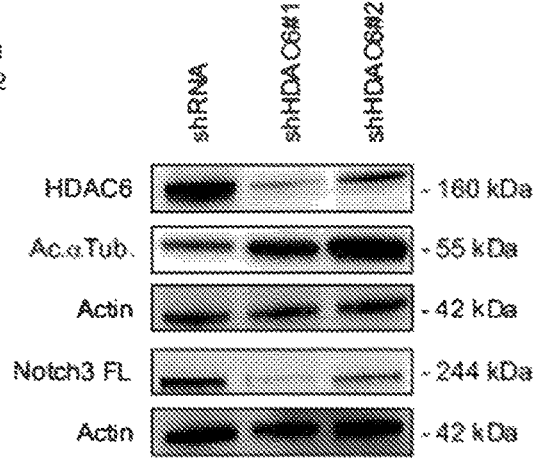 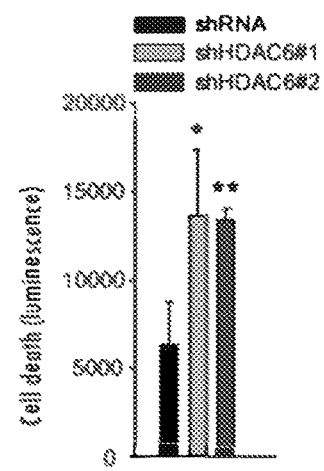
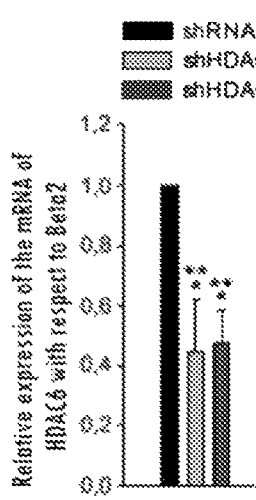 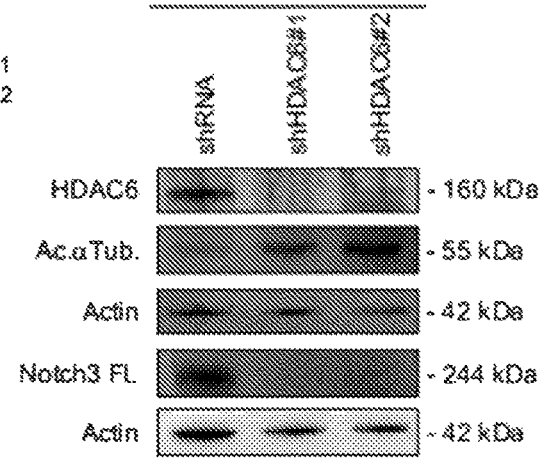 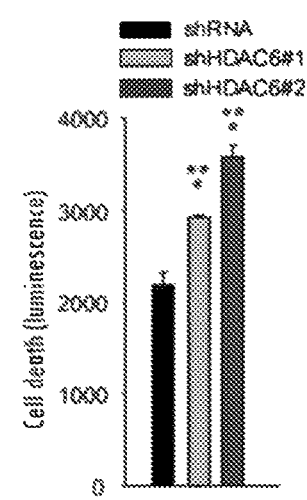
Fig. 6A   Fig. 6B   Fig. 6C

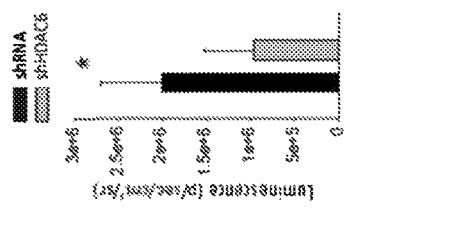
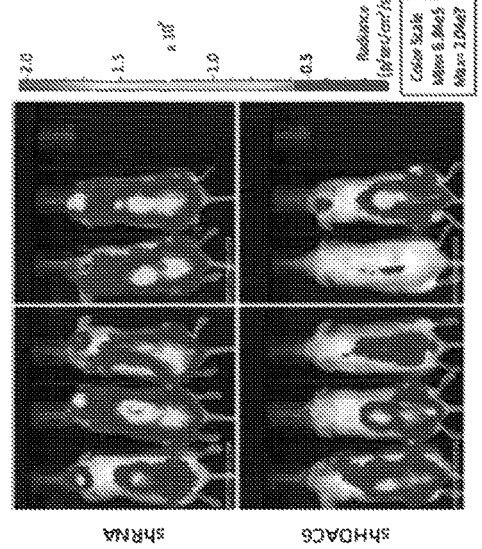
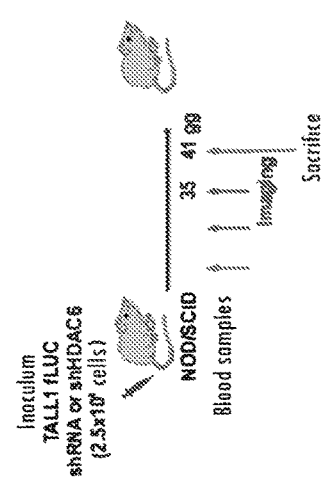
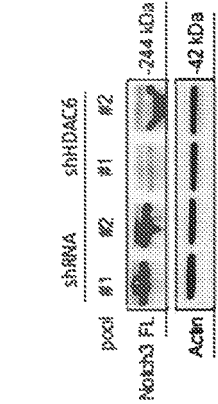
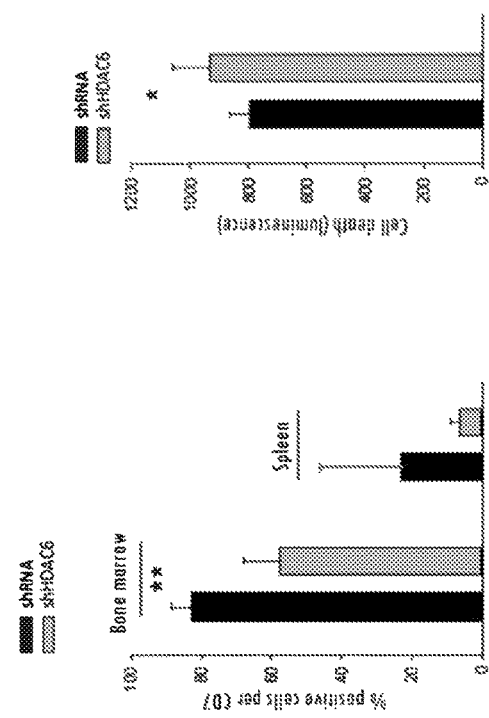
Fig. 7A  Fig. 7B  Fig. 7C  Fig. 7D  Fig. 7E  Fig. 7F

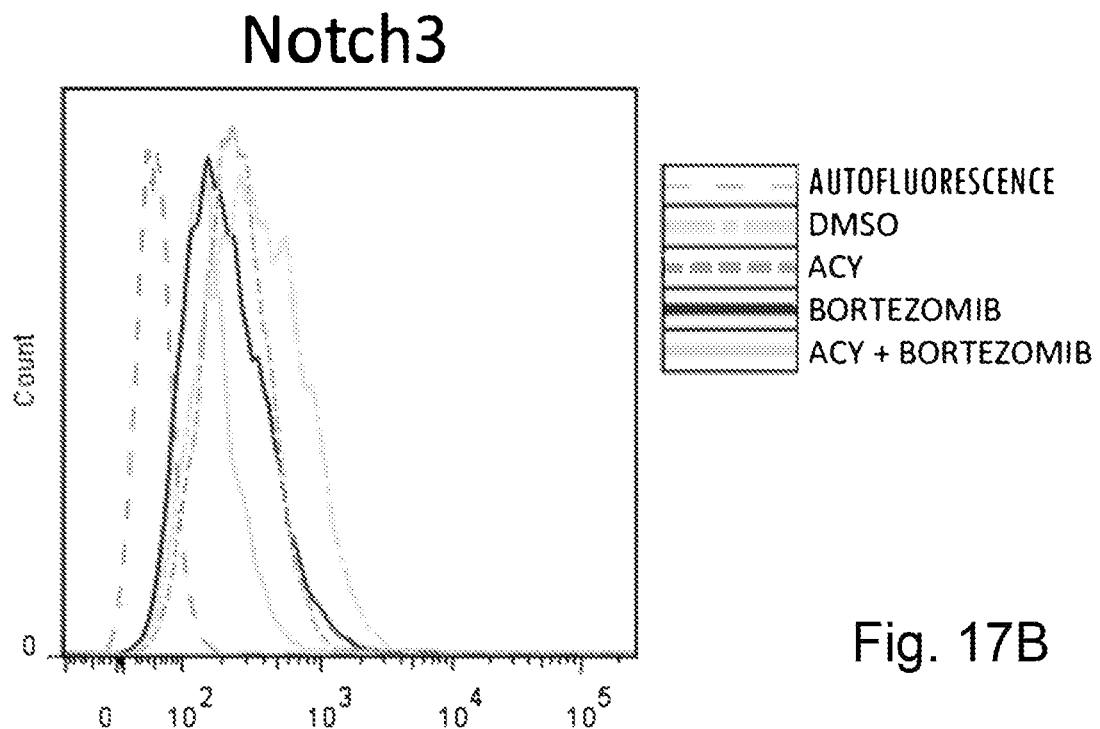
Fig. 17B
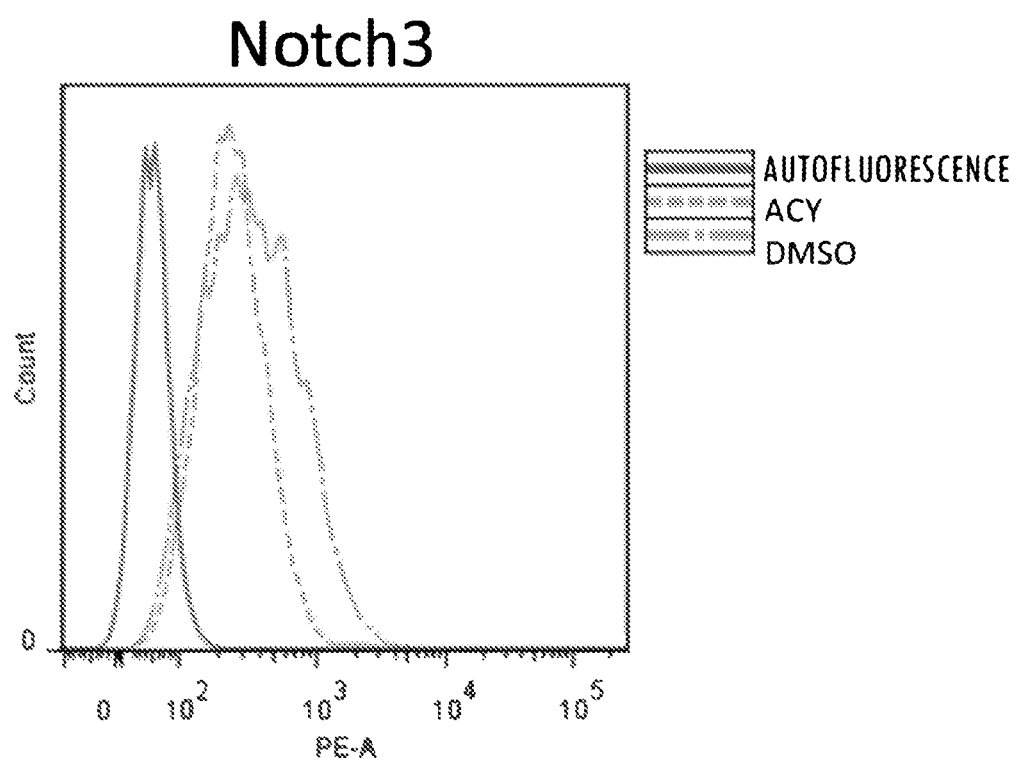

INHIBITOR OF HISTONE DEACETYLASE 6 IN THE TREATMENT OF T-CELL ACUTE LYMPHOBLASTIC LEUKEMIA (T-ALL) AND OTHER NEOPLASIA WITH HIGH EXPRESSION OF NOTCH-3

CROSS-REFERENCE TO RELATED APPLICATIONS

This application is a U.S. National Phase filing of PCT International Patent Application No. PCT/IB2018/055605, having an international filing date of Jul. 26, 2018, which claims priority to Italian Patent Application No. 102017000086293, filed Jul. 27, 2017 each of which is hereby incorporated by reference in its entirety.

FIELD OF THE INVENTION

T-cell acute lymphoblastic leukemia (T-ALL) is a cancer characterized by the clonal expansion of T-lymphocyte precursors.

BACKGROUND OF THE INVENTION

T-ALL represents 15% of pediatric leukemia and 25% of adult leukemia and is characterized by an unfavorable prognosis compared to the more common B-ALL (1).

Although the majority (75%) of pediatric patients affected by T-ALL are treated effectively using current treatment protocols, about a quarter of patients show resistance to therapy or experience relapses.

Notch receptors are type I trans-membrane glycoproteins, highly conserved among different species, which regulate important cell functions such as proliferation, differentiation, preservation of staminality and cell survival in different tissues.

Following the activation of the receptor, there is a conformational change leading to two sequential proteolytic cuts that release the intracellular portion (ICD), which migrates into the nucleus and activates the transcription of target genes.

Various indications at the cytogenetic, molecular and genomic levels have shown that 50-60% of T-ALL patients have aberrant activation of the Notch1 receptor signaling pathway, due to mutations in this gene (2).

Moreover, it has been previously reported that the forced expression of the intracellular domain of the Notch3 receptor (Notch3-ICD) is also capable of inducing the development of leukemia in mice and that increased expression of this receptor is commonly found in human T-ALLs, although mutations in Notch3 are rare (3, 4).

The lack of mutations in Notch3 suggests a possible epigenetic regulation of this receptor, linked to changes in the DNA structure and not so much to changes in its sequence.

Numerous studies have shown that the formation of endocytic vesicles regulates the activity of the Notch receptors and the ligands thereof (5).

In *Drosophila*, Notch endocytosis, mediated by dynamin, facilitates the dissociation of the heterodimer and the exposure of the cut site in the cell receiving the signal (6-7). The activated receptor, together with the ligands and the non-active receptor, is then internalized to the cell and diverted into the sorting endosomes, where the fate of these proteins will be decided: the re-emission of the receptor in the membrane or the degradation thereof by lysosome. This internalization process seems to be important for modulating the activity of the signaling pathway, controlling the amount of Notch receptor on the cell surface and preventing the inappropriate activation thereof in the absence of ligand (8). Intracellular traffic to the endosomal/lysosomal compartments is moreover associated with attenuation of Notch signaling (9). In this regard, the study by Jia et al. reports the degradation by lysosome of the Notch3 receptor, both in the whole form and in the active form in some human cancer lines. This mode of degradation appears to be specific to Notch3, contrary to what is seen for Notch1 and Notch4, which are preferentially degraded through proteasome (10).

Histone deacetylases (HDACs) are a family of proteins known primarily for their role in regulating the DNA structure, influencing acetylation of histones and consequently the level of gene expression. However, alongside this function within the nucleus, some HDACs are located in the cytoplasm of the cell and modify non-histonic structural proteins (11). These include HDAC6, the histone deacetylase that regulates the acetylation of α-tubulin, an important structural protein that forms microtubules, a complex network of "cavities" that maintain the shape and three-dimensionality of cells and on which flow all the vesicles containing proteins that need to be moved inside the cell. In particular, inhibition of HDAC6 leads to an increase in α-tubulin acetylation and consequently an increase in vesicular transport speed (12). In this regard, it has already been described that HDAC6 regulates vesicular traffic and EGFR degradation by modulating the state of acetylation of the tubulin (13, 14).

Numerous studies have shown that histone deacetylases play a fundamental role in cancer development and progression and over the years numerous more or less specific inhibitors (HDACi) against these proteins have been developed. HDACi have demonstrated since the beginning in laboratory experiments a high toxicity to cancer cells, but not to healthy cells, making them potential candidates as new anti-cancer drugs. Some of these inhibitors have entered clinical practice for the treatment of hematological neoplasia. In particular, three pan-HDACi (Vorinostat, Belinostat, Romidepsin), capable of inhibiting various HDACs including HDAC6, have been approved by the FDA for the first-line treatment of cutaneous or peripheral T-cell lymphoma (PTCL/CTCL) (15). Recently, Panobinostat was approved for the treatment of multiple myeloma in combination with Bortezomib and Dexamethasone (16), but side effects such as diarrhea, thrombocytopenia and asthenia remain relevant, probably due to the simultaneous blocking of various HDACs.

The two pathways that have been pursued so far include (I) the use of Gamma Secretase Inhibitor (GSI), which blocks the second proteolytic cut of the activated receptor, and (II) monoclonal antibodies against Notch (17).

GSIs, despite encouraging in vitro data, have encountered many difficulties in clinical trials due to high intestinal toxicity, hypothetically due to the simultaneous blocking of various Notch receptors expressed by the intestinal mucosa.

As far as antibodies are concerned, their clinical development is less advanced than that of GSIs and there is still no mature data on their toxicity, even though they would still have the inconvenience of requiring to be administered intravenously, with the patient needing access to a day-hospital and, therefore, involving higher costs than with drugs taken orally.

There is therefore a need to identify new therapies for neoplasia, in particular T-cell acute lymphoblastic leukemia (T-ALL) which overcome the drawbacks of the therapies available today.

SUMMARY OF THE INVENTION

As its first object, the present invention discloses compounds for use in the treatment of neoplasia.

In a preferred aspect, these neoplasia are represented by T-cell acute lymphoblastic leukemia (T-ALL), as well as other neoplasia with high Notch 3 expression.

In particular, such compounds are represented by histone deacetylase 6 inhibitors (HDAC6).

In a further aspect, a method for treating neoplasia is described comprising the administration of the compounds of the invention.

BRIEF DESCRIPTION OF THE FIGURES

FIGS. 6A-6C shows the results of in vitro genetic inhibition of HDAC6;

FIGS. 7A-7F shows the results of HDCA6 genetic inhibition in preclinical T-ALL mouse models;

Figure 18:
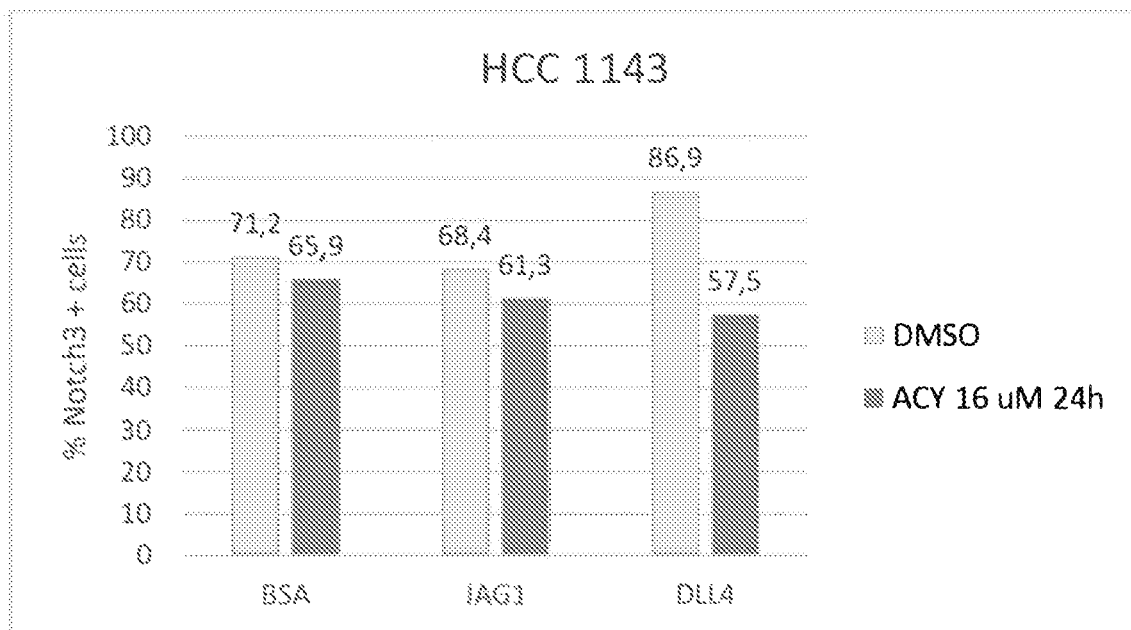
Figure 18:
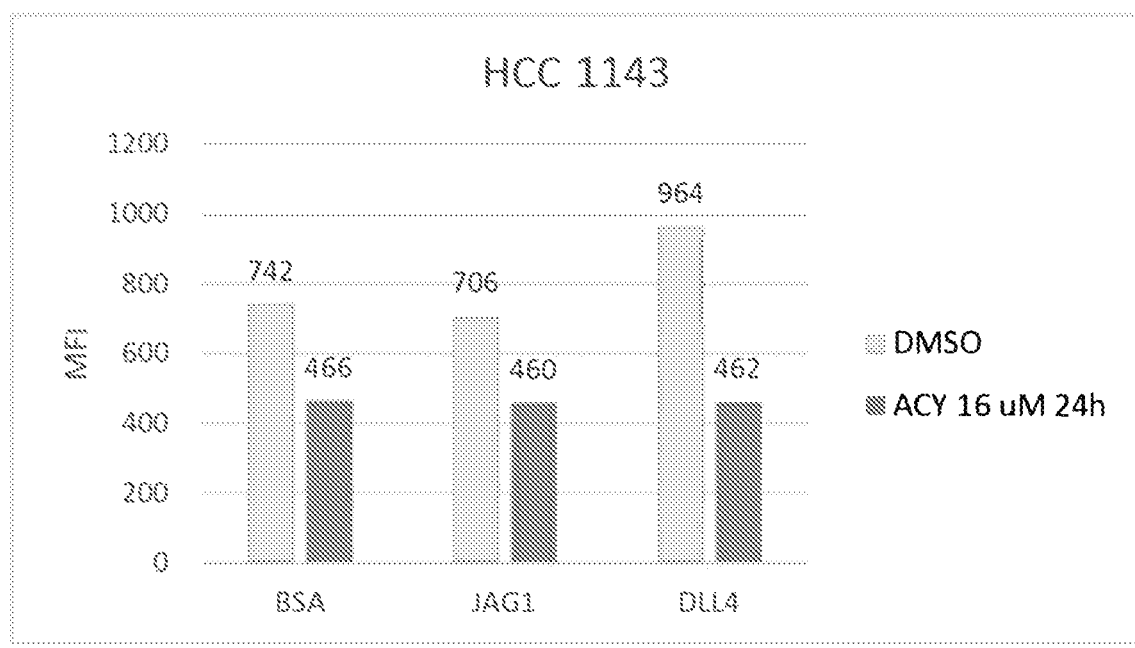
Figure 19:
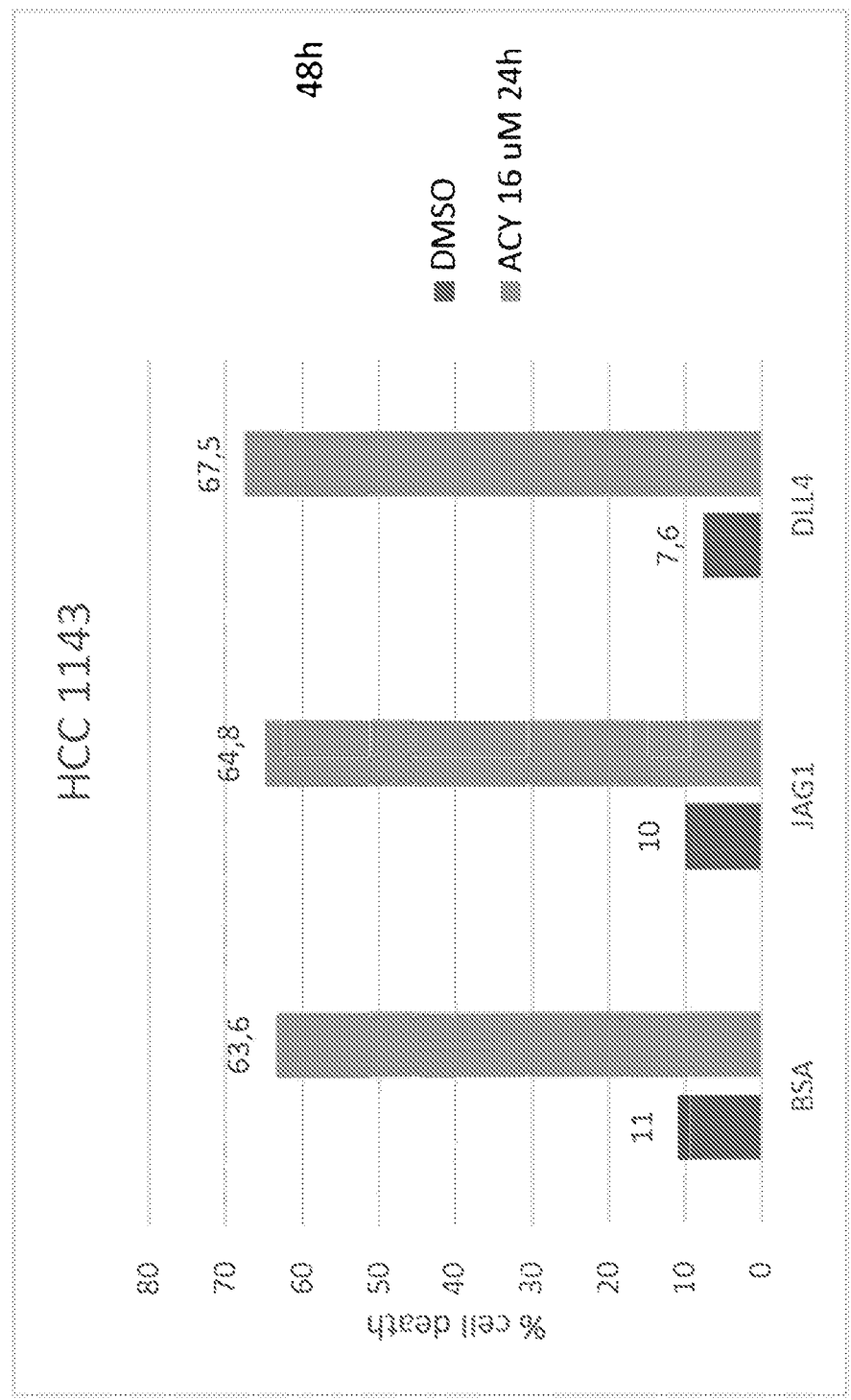

the graphs in FIGS. 17A-17B show the results of the evaluation of Notch3 membrane expression in HCC-1143 cells treated with rocilinostat and/or bortezomib;

FIG. 18 shows the results of the cytofluorometric evaluation of Notch3 expression after treatment with rocilinostat in the presence of Notch ligands (HCC-1143);

FIG. 19 shows the results of the evaluation of cell mortality induced by rocilinostat in MCC-1143 cells.

DETAILED DESCRIPTION OF THE INVENTION

As mentioned above, according to a first object, the present invention discloses compounds for use in the treatment of neoplasia.

More specifically, such compounds are represented by histone deacetylase enzyme inhibitors of subclass 6 (HDAC6).

Such compounds are selected from the group comprising: ricolinostat (ACY-1215, Celgene, marketed by Sellckchem), ACY-241 (Celgene), KA2507 (Karus Therapeutics Limited).

For the purposes of the present invention, the compounds described find application for the treatment of neoplasia characterized by:

NOTCH3 gene mutations or amplification; and/or high expression of the NOTCH3 gene and/or NOTCH1 gene mutations.

Thus, a patient who may be treated with the compounds of the invention is a patient having:

NOTCH3 gene mutations or amplification; and/or high expression of the NOTCH3 gene and/or NOTCH1 gene mutations.

In a preferred aspect of the present invention, the neoplasia that may be treated are represented by T-cell acute lymphoblastic leukemia (T-ALL).

More specifically, the present invention makes compounds available for the treatment of acute lymphoblastic T-cell leukemia (T-ALL) in a patient, wherein said patient has one of the following conditions:

NOTCH3 gene mutations or amplification; and/or high expression of the NOTCH3 gene and/or NOTCH1 gene mutations.

According to a first aspect, the compounds are described for the treatment of an adult patient.

In an alternative embodiment, the invention finds application in the treatment of a pediatric patient.

More specifically, a pediatric patient is under 15 years of age.

Another aspect describes a method for treating neoplasia that includes the administration of the compounds of the invention, either alone or in combination with other drugs.

According to a further embodiment, the compounds of the invention may be used in combination with other drugs.

For example, this may involve:
1) proteasome inhibitors;
2) steroidal anti-inflammatory drugs;
3) chemotherapeutics.

In particular, proteasome inhibitors are for example represented by bortezomib.

As far as steroidal anti-inflammatory drugs are concerned, these are selected from the group comprising: dexamethasone and prednisone.

For the purposes of the present invention, the compounds described may be administered orally.

In particular, the therapy consists of one or more treatment cycles, each lasting about 21 days.

The administration of drugs within a treatment cycle takes place from day 1 to day 5 and from day 8 to day 12.

The amount of compound administered is about 150-170 mg/day, preferably about 160 mg/day.

In one aspect of the invention, in a first course of treatment, the drug Bortezomid is administered intravenously at a dose of approximately 1.3 mg/m$^2$ twice a week for two weeks (e.g. on days 1, 4, 8 and 11).

Prednisone is administered orally at a dose of approximately 40-120 mg/m$^2$ per day on days 1-5 (with a 21-day cycle).

Dexamethasone is administered orally at a dose of approximately 40 mg/m$^2$ daily on days 1-4 and 9-12 (with a 21-day cycle).

In a further embodiment, the present invention describes a method for treating neoplasia comprising the administration of the compounds of the invention as described above.

Such compounds are administered to a patient in need thereof in a pharmacologically effective dose.

In a preferred aspect, these neoplasia are represented by T-cell acute lymphoblastic leukemia (T-ALL), as well as other neoplasia with high Notch 3 expression.

In particular, such compounds are represented by histone deacetylase 6 inhibitors (HDAC6), which are preferably chosen from the group comprising: ricolinostat (ACY-1215, marketed by Sellckchem) (Celgene), ACY-241 (Celgene), KA2507 (Karus Therapeutics Limited).

In a particularly preferred aspect of the invention, the patient is one in whom one or more of the following conditions have been ascertained:
a) NOTCH3 gene mutations or amplification; and/or
b) high expression of the NOTCH3 gene and/or
c) NOTCH1 gene mutations.

Materials and Methods

Initially we treated 3 T-ALL cell lines in the laboratory with Tricostatin A (TSA), a generic commercial inhibitor that inhibits the whole class of HDACs that is commonly used in experimental practices. We demonstrated that this inhibitor leads to a significant reduction in Notch3 receptor protein levels in all cell lines tested and, consequently, in Notch-regulated genes. The same result was obtained by treating 7 patient-derived primary lines in vitro with TSA. The reduction of Notch3 levels at the cell membrane level in one of these T-ALL lines has also been demonstrated.

Figure 1A:
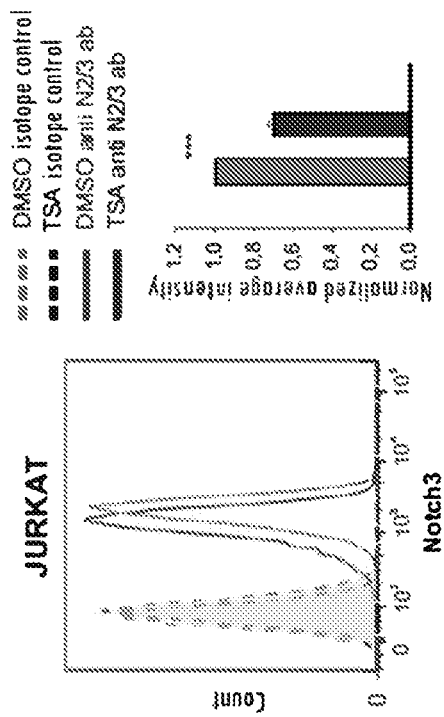
FIGS. 1A-1E shows the results of experiments conducted with the generic inhibitor TSA.
Figure 1B:
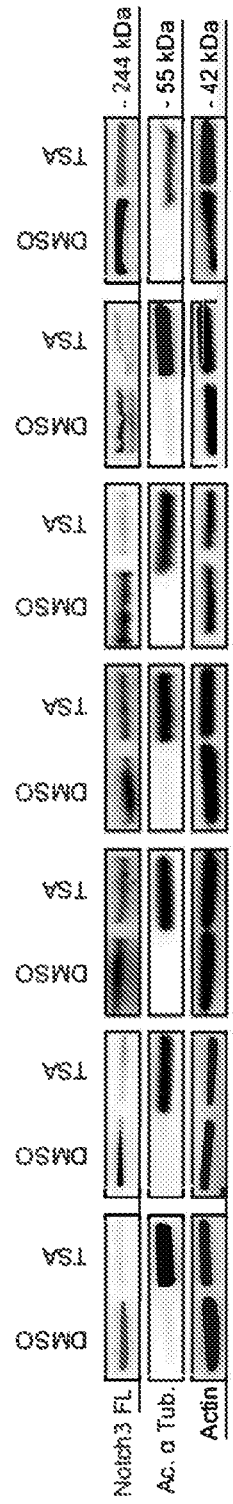
Figure 1C:
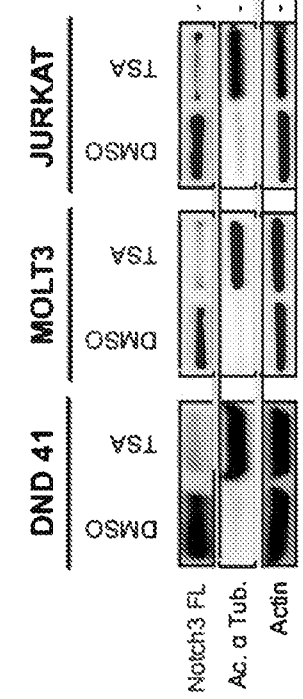
Figures 1D, 1E:
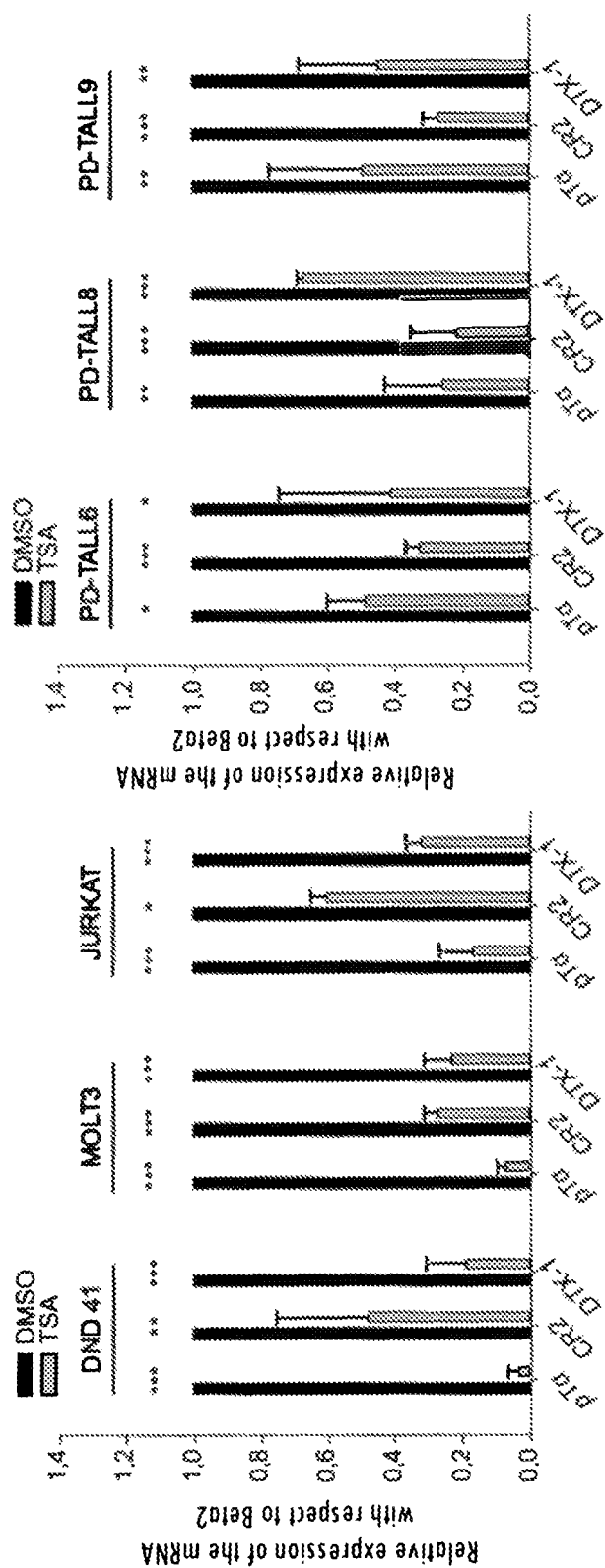

In particular, in FIG. 1A is shown the three cell lines of T-ALL MOLT3, Jurkat and DND41 were treated for 16 hours in vitro with TSA 500 nM. The western blotting confirms the decrease of the full length (FL) Notch3 receptor after treatment. Inhibition of HDACs is confirmed by the increase of acetylated tubulin (Ac. α Tub.). FIG. 1B shows the decrease of the Notch3 receptor present in the membrane was confirmed in the Jurkat cells by marking the cells with a Notch2/3 antibody and subsequent analysis with the cytofluorometer. In FIG. 1C, n=7 patient-derived primary lines were treated in vitro for 16 hours with TSA 500 nM, confirming the result seen in the cell lines. The treatment with TSA is accompanied by a decrease in the target genes pTα, CR2, DTX-1 in the cell lines shown in FIG. 1D and in the primary cells shown in FIG. 1E. ($*P<0.05$, $P<0.01$, $*P<0.001$, mean±SD of three independent experiments).

Treatment with TSA is accompanied by some functional effects such as inhibition of proliferation and induction of cell death of treated leukemic cells, confirming the fundamental role of Notch3 in T-ALL. Cell death is due to the decrease in Notch3 because, by restoring the protein levels of this receptor, the cells treated with TSA die significantly less.

Figure 2B:
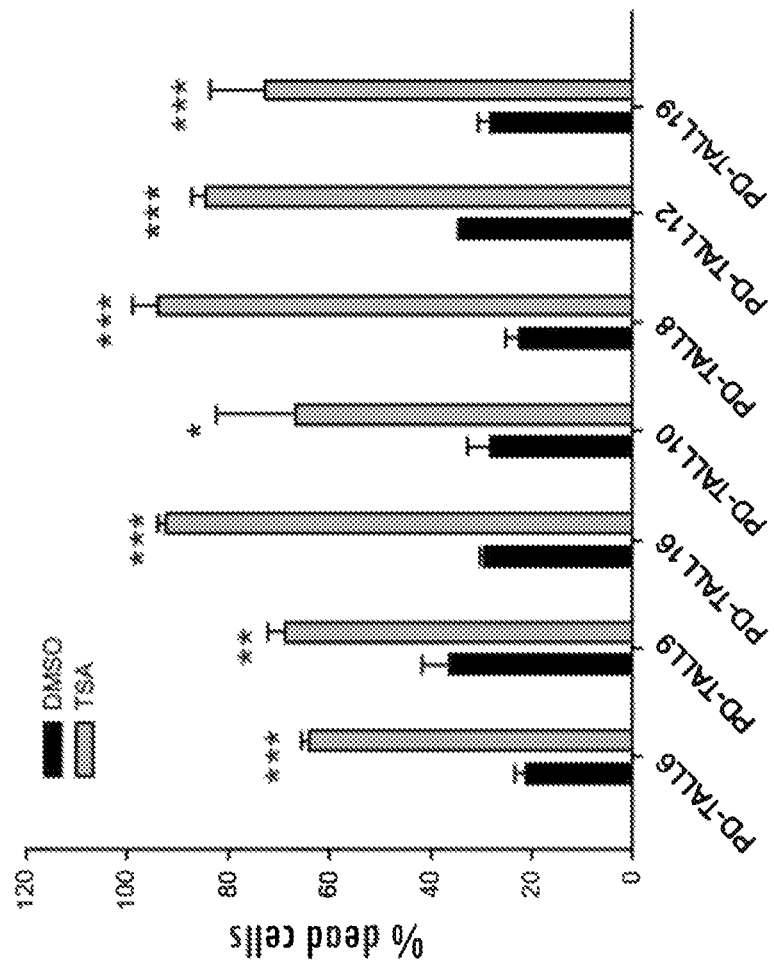
FIGS. 2A-2D shows the results of HDAC inhibition on cell proliferation and apoptosis.
Figure 2A:
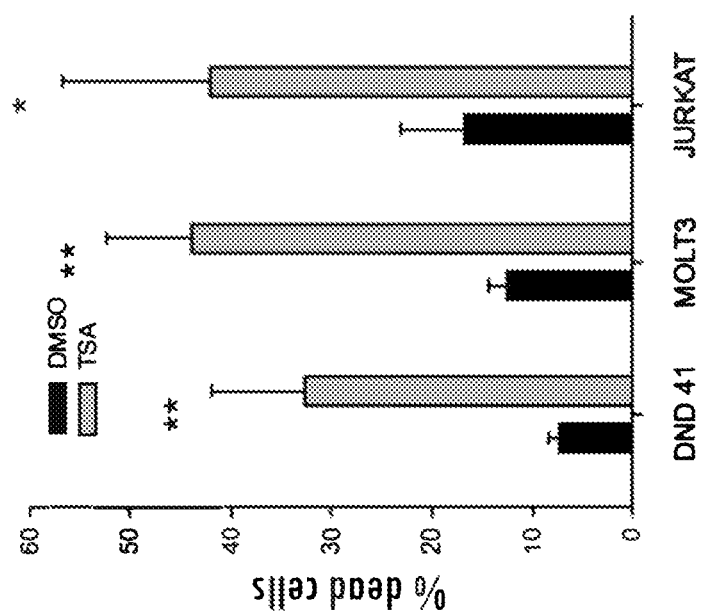
Figure 2C:
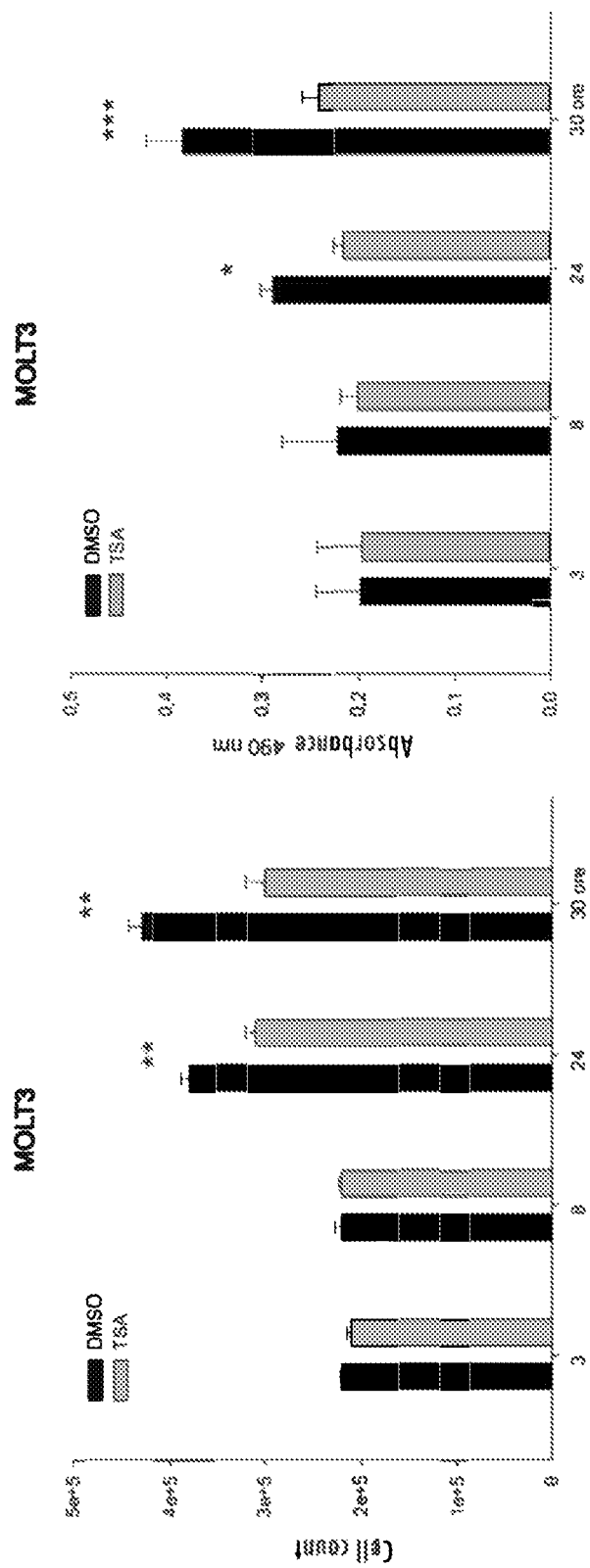
Figure 2D:
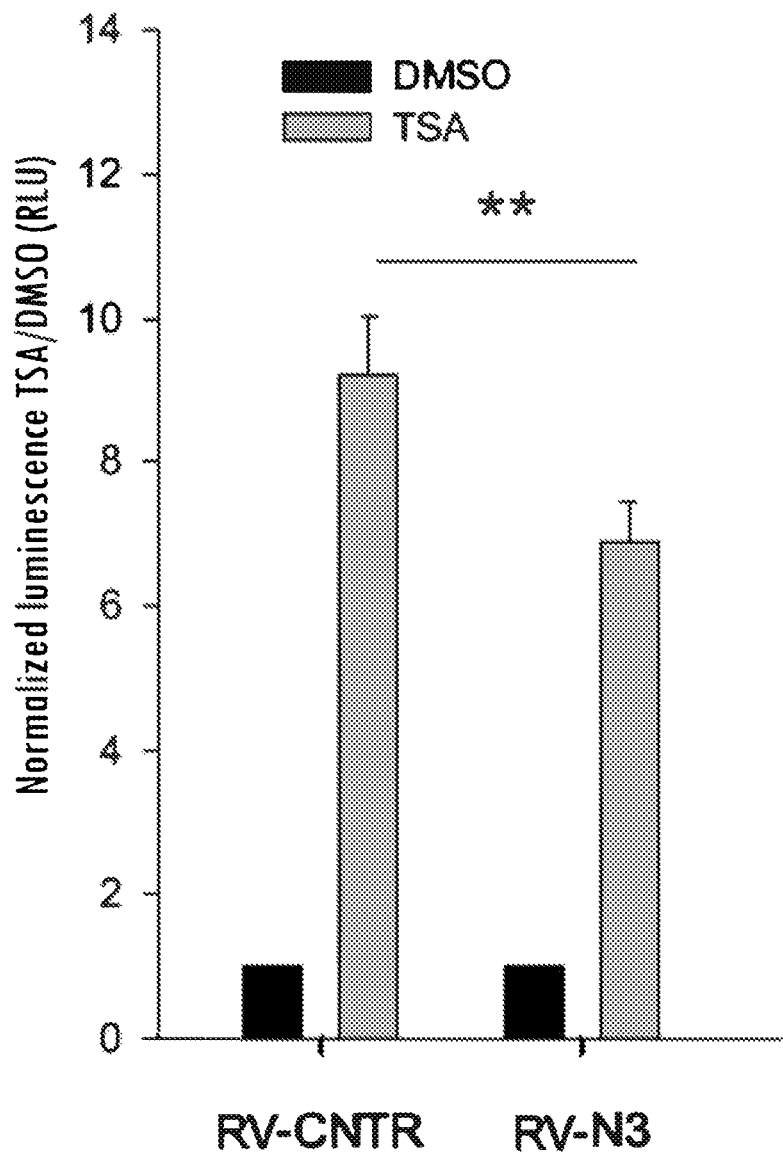

In FIG. 2A and the 7 primary lines shown in FIG. 2B were treated for 24 hours in vitro with TSA 500 nM. Cell death was evaluated by marking with annexin V and analysis with the cytofluorometer. Proliferation inhibition shown in FIG. 2C was assessed in the MOLT3 line by cell count (left panel) and MTS assay (right panel). In FIG. 2D, the Jurkat cells were infected with a control virus (RV-CNTR) or with an expressing Notch3 virus (RV-N3) and subsequently treated with TSA 500 nM for 24 hours. Cell death was evaluated by a luminescence assay for caspase activation ($*P<0.05$, $P<0.01$, $*P<0.001$, mean±SD of three independent experiments).

Subsequently it was demonstrated that the decrease in protein levels is due to the degradation of this receptor through the lysosome, a highly acidic organelle used for destroying proteins. TSA treatment is in effect accompanied by an increase in co-localization between Notch3 and LAMP2, a protein present in lysosomes. It is interesting to note that the simultaneous use of TSA and the MG132 proteasome inhibitor leads to a further decrease in the protein levels of Notch3 present on the cell membrane, suggesting the possibility of combining HDAC and proteasome inhibitors (for example Bortezomib, already used in practice) to further reinforce the negative effect on the receptor.

Figures 3A, 3B:
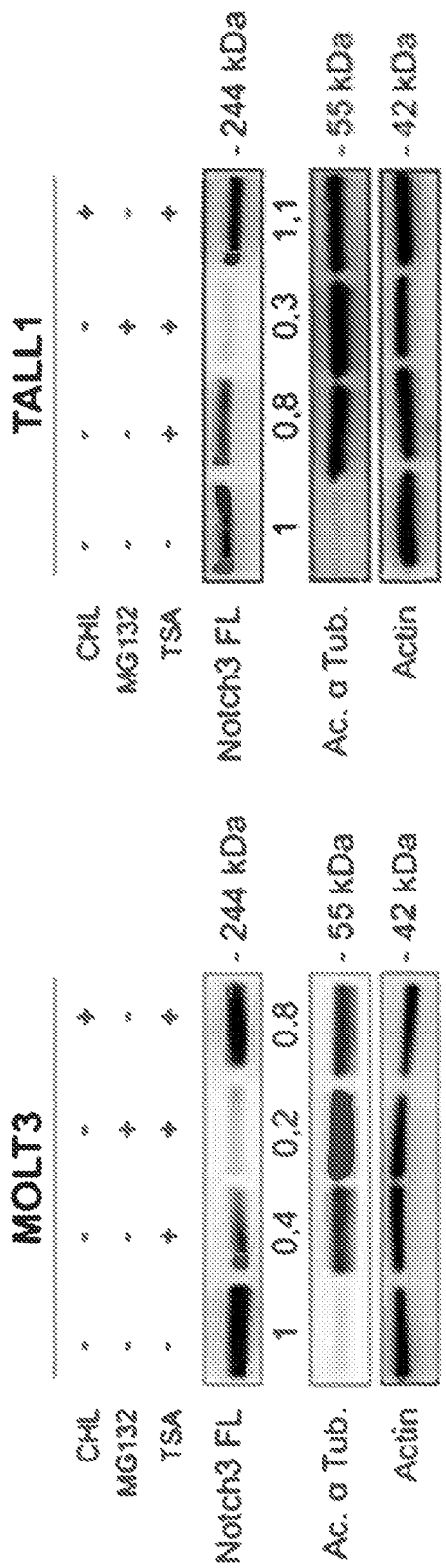
FIGS. 3A-3D shows the results of treatment of MOLT3 and T-ALL1 cells with TSA, lysosome and proteasome inhibitors.
Figure 3C:
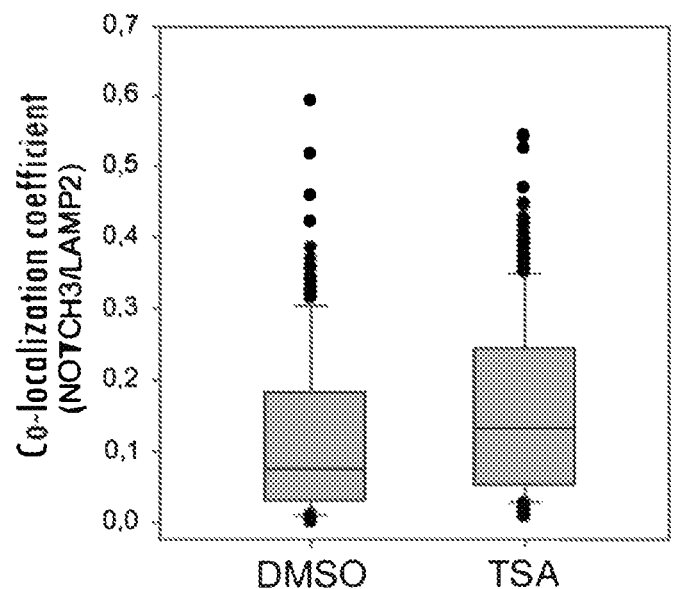
Figure 3D:
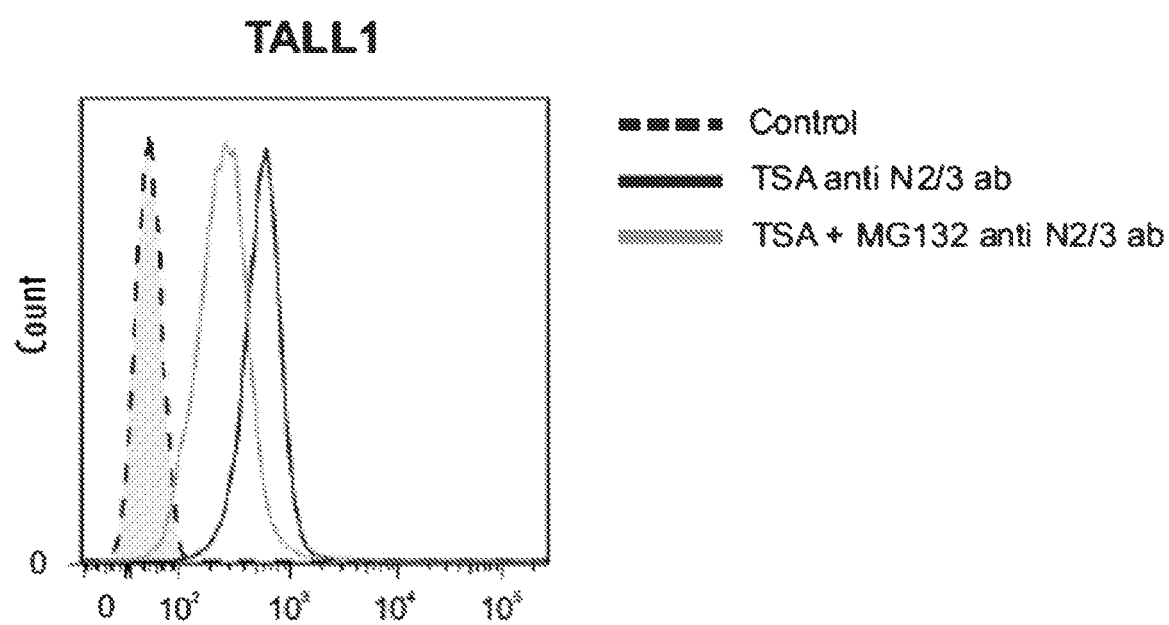

MOLT3 cells shown in FIG. 3A and TALL1 cells shown in FIG. 3B were treated with TSA 500 nM for 16 hours, and simultaneously in the presence or absence of a proteasome (MG132) or lysosome (chloroquine—CHL) inhibitor. Only by inhibiting the lysosome using Chloroquine is the decrease of Notch3 blocked. Blocking the proteasome, on the other hand, further lowers Notch3 protein levels. The numbers below the bands refer to densitometric analysis. FIG. 3C provides the increase in co-localization between Notch3 and the lysosomal marker LAMP2 after treatment with TSA, by immunofluorescence analysis ($***p<0.001$, N=21 cells analyzed for each condition). Using TSA+MG132 leads to a greater decrease in the Notch3 receptor present in the membrane compared to TSA alone shown in FIG. 3D.

To understand which HDAC is responsible for the effect, the T-ALL cells were treated with several HDAC1-, 6- and 8-specific inhibitors, and we observed that only by inhibiting HDAC6 using Tubacin are effects comparable to the generic TSA inhibitor, both with regard to cell death and the decrease in Notch3 protein levels and downstream target genes.

Figure 4A:
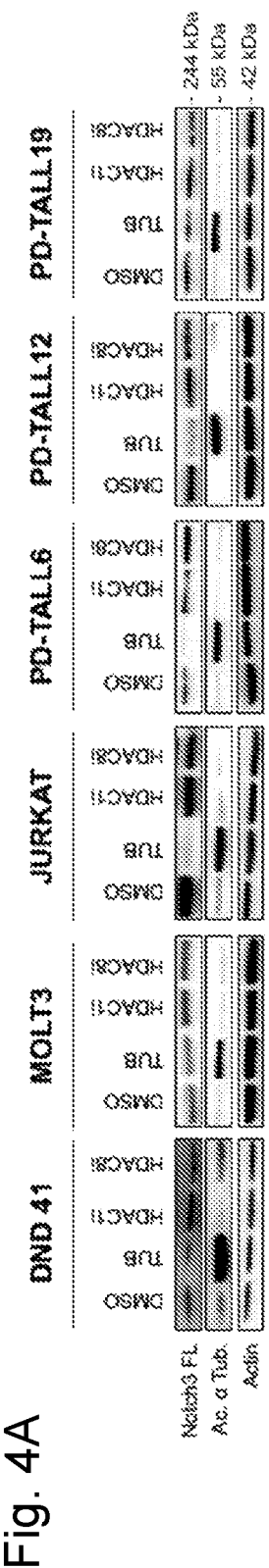
FIGS. 4A-4C shows the results of in vitro pharmacological inhibition of HDAC6 on protein levels and apoptosis.
Figure 4B:
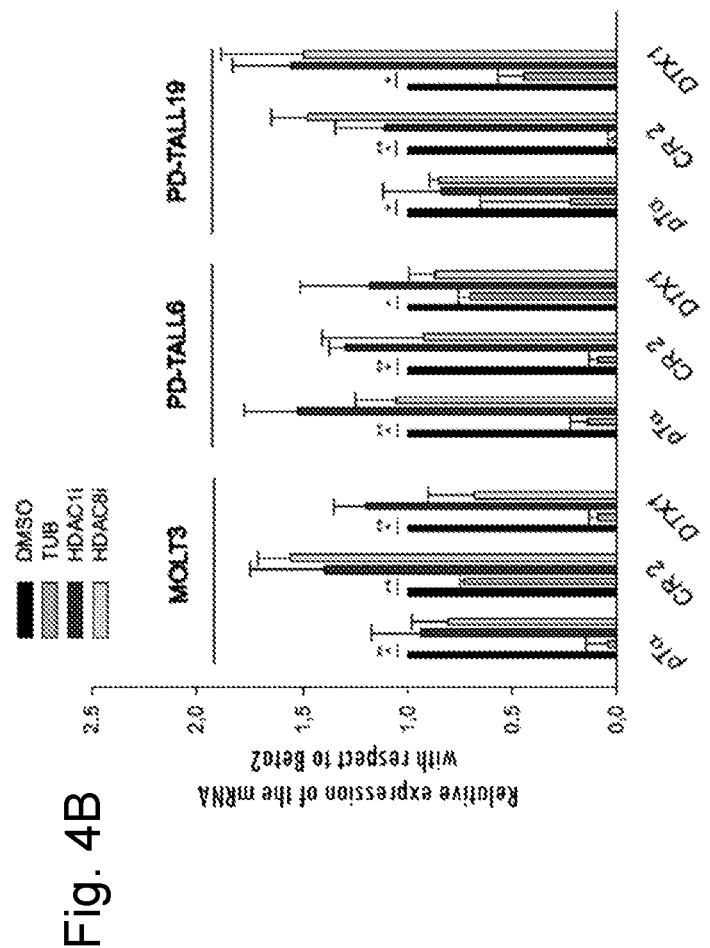
Figure 4C:
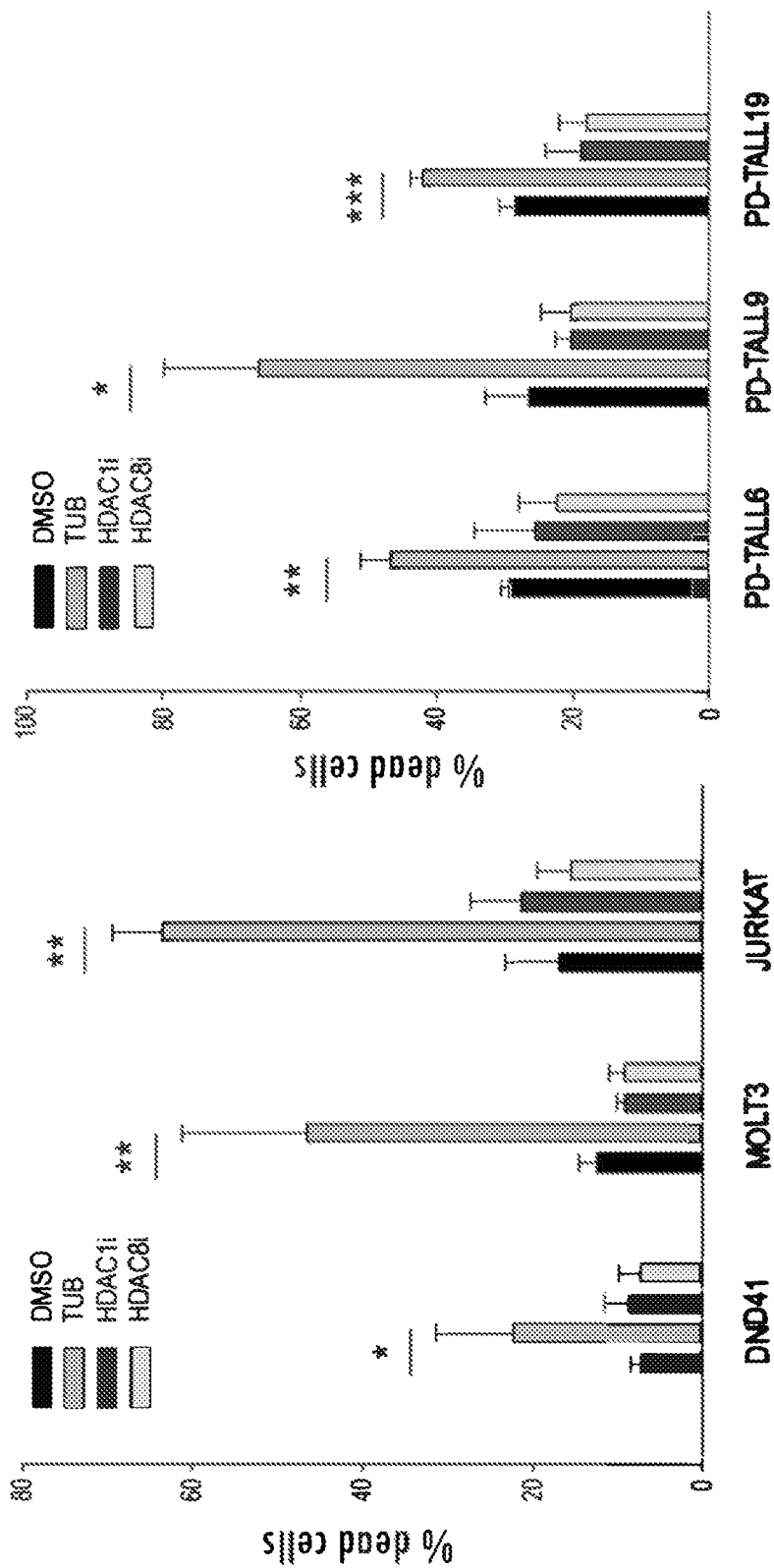

In FIG. 4A, T-ALL cell lines and primary cells were treated in vitro for 16 hours with the HDAC6 inhibitor Tubacin (2 μM, TUB), HDAC1 inhibitor (2 μM, HDAC1i), or HDAC8 inhibitor (2 μM, HDAC8i). Treatment with Tubacin is shown in FIG. 4B, but not with the other inhibitors, is accompanied by a decrease in the target genes pTα, CR2, DTX-1. In FIG. 4C, the three cell lines of T-ALL MOLT3, Jurkat and DND41 (left) and n=3 primary lines (right) were treated for 24 hours in vitro with the compounds previously described, and cell death was evaluated by marking with Annexin V and analysis by cytofluorometer ($*P<0.05$, $P<0.01$, $*P<0.001$, mean±SD of three independent experiments).

It is interesting to note how the TALL1 cell line, which is known to be highly dependent on Notch3, is significantly more sensitive to inhibition of HDAC6 with Tubacin than the other cell lines analyzed.

Figure 5:
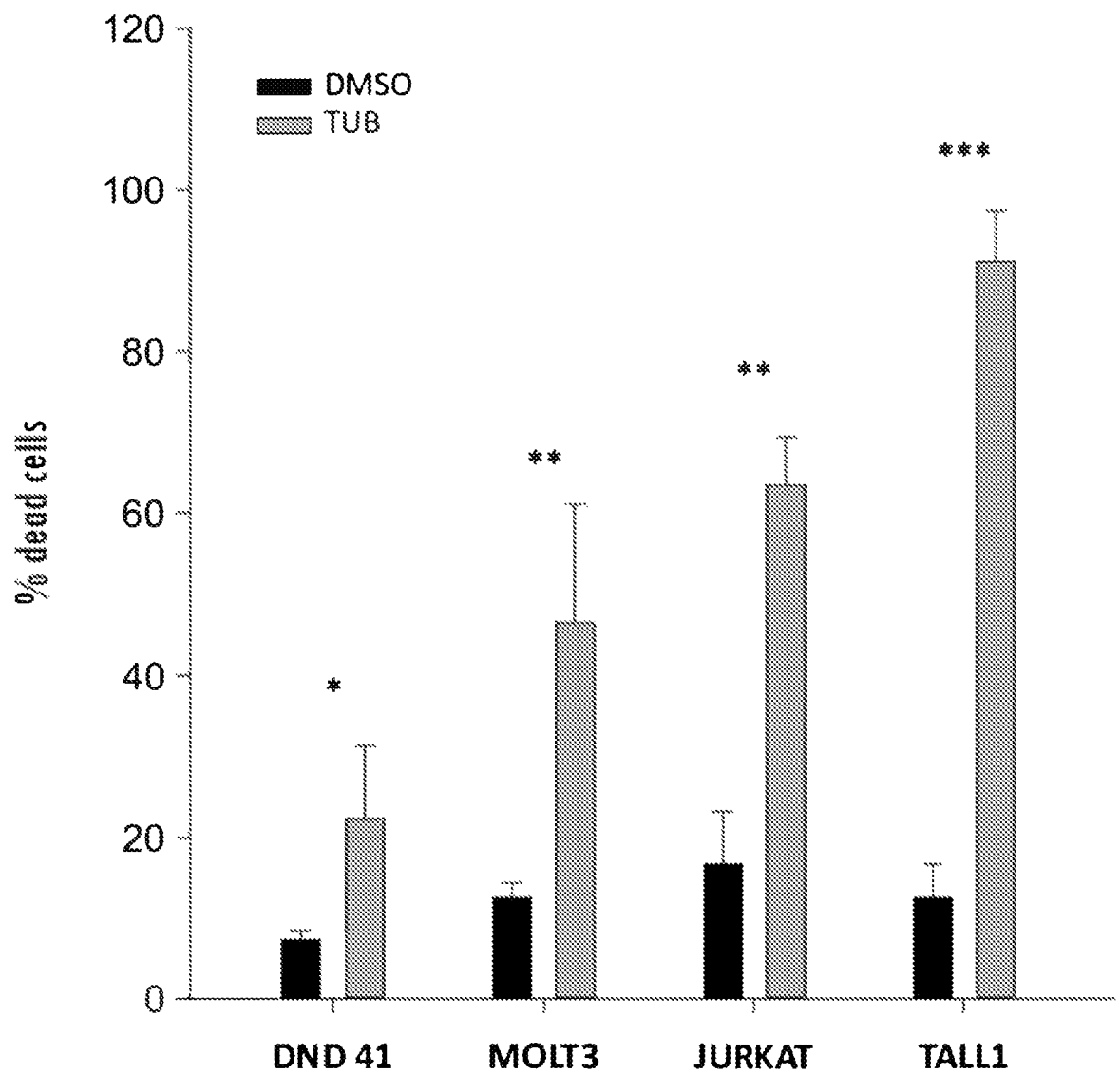
FIG. 5 shows the results of in vitro pharmacological inhibition of HDAC6 on protein levels and apoptosis on T-ALL1 cells compared to other cell lines.

In FIG. 5 the T-ALL cell lines were treated in vitro for 24 hours with the HDAC6 Tubacin inhibitor (2 μM, TUB) and cell death was assessed by marking with Annexin V and analysis by cytofluorometer ($*P<0.05$, $P<0.01$, $*P<0.001$, mean±SD of three independent experiments).

Since specific drug inhibitors may still have low affinity for other non-specific targets as well, in order to rule out off-target effects of Tubacin, we reduced the expression of HDAC6 in cells using the short-interfering RNA (shRNA) method. Also in this case, the reduction in the amount of active HDAC6 in the cell resulted in a reduction of Notch3 protein and a consequent increase in death.

In FIGS. 6A-6C, MOLT3 and TALL1 cell lines were infected with two different lentiviruses that block HDAC6 expression (shHDAC6 #1 and #2). The actual decrease of HDAC6 was confirmed at the level of mRNA as shown in FIG. 6A and of protein shown in FIG. 6B. In FIG. 6B, HDAC6 silencing is accompanied by a decrease in protein levels in Notch3 and an increase in death, measured by a luminescence assay for caspases shown in FIG. 6C (*P<0.05, P<0.01, *P<0.001, mean±SD of three independent experiments).

Finally, we have demonstrated the dependence of Notch3 protein levels on HDAC6 inhibition even in preclinical T-ALL models. In particular, we have demonstrated that the reduction of HDAC6 in leukemic mice with high Notch3 levels resulted in a decrease in Notch3 protein levels, reduced tumor growth and increased cell death, confirming the therapeutic effect also in vivo.

TALL1 leukemic cells, highly dependent on the Notch3 signaling pathway, were inoculated into mice and the development of the disease was monitored (see FIG. 7A. The mice with HDAC6 reduction (shHDAC6) presented a lower positive signal for leukemia than the cells wherein HDAC6 is present at normal levels (shRNA) shown in FIG. 7B. This difference is significant, as shown in FIG. 7C, wherein the averages of the signal intensities are represented. Moreover, at the time of sacrifice there is a reduced infiltration of the bone marrow by the leukemic cells shown in FIG. 7D and an increase in death shown in FIG. 7E. The reduction of HDAC6 is accompanied also in this model by a reduction of Notch3 protein shown in FIG. 7F (*P<0.05, P<0.01, *P<0.001, n=5 mice/group).

Another series of experiments were performed in vitro using T-ALL or breast cancer lines characterized by high expression of Notch3.

It should be noted that the results of treatments with rocilinostat have been evaluated in biochemical terms, by Western blot analysis, or by cytofluorometry and cell viability and proliferation assays.

Figure 8C:
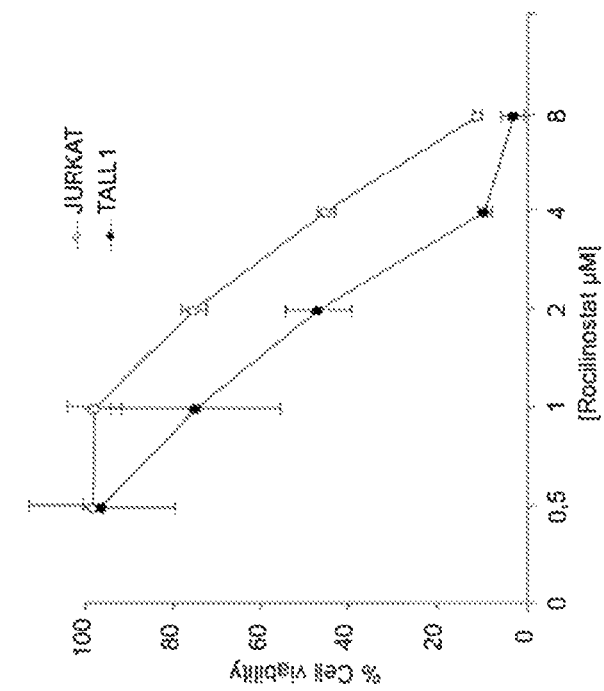
FIGS. 8A-8C shows the results of some assays carried out to verify the effects of rocilinostat in T-ALL cells.
Figure 8B:
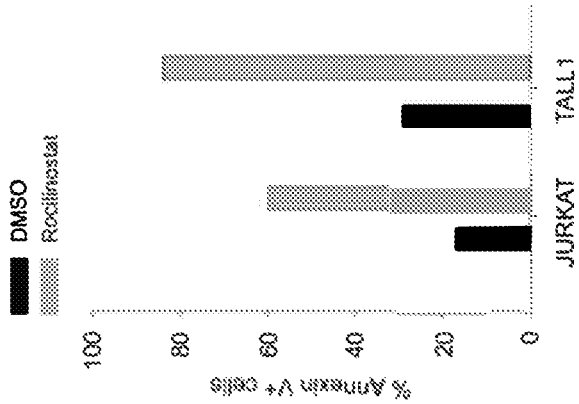
Figure 8A:
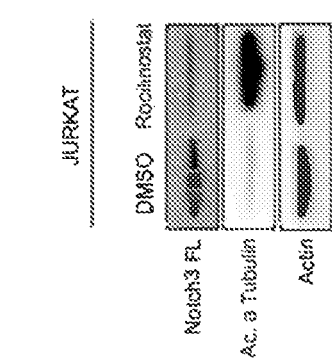

In FIG. 8A, JURKAT cells were treated in vitro with rocilinostat at a concentration of 8 $\mu$M for 16 hours. Analysis of cellular lysates using Western blotting indicates that treatment with this HDAC6i decreases levels of the NOTCH3 FL protein. The increase in acetylated tubulin levels confirms the biochemical activity of rocilinostat; Evaluation of apoptosis in JURKAT and TALL1 after 24 hours of treatment with rocilinostat (8 $\mu$M) is shown in FIG. 8B: the assay of annexin V indicates that there is a strong increase of cell death associated with HDAC6 inhibition; Evaluation of cell viability by the ATPlite assay in two T-ALL cell lines after 48 hours of treatment with rocilinostat at the indicated concentrations is shown in FIG. 8C: a marked negative effect on cell growth is evident.

Figure 9:
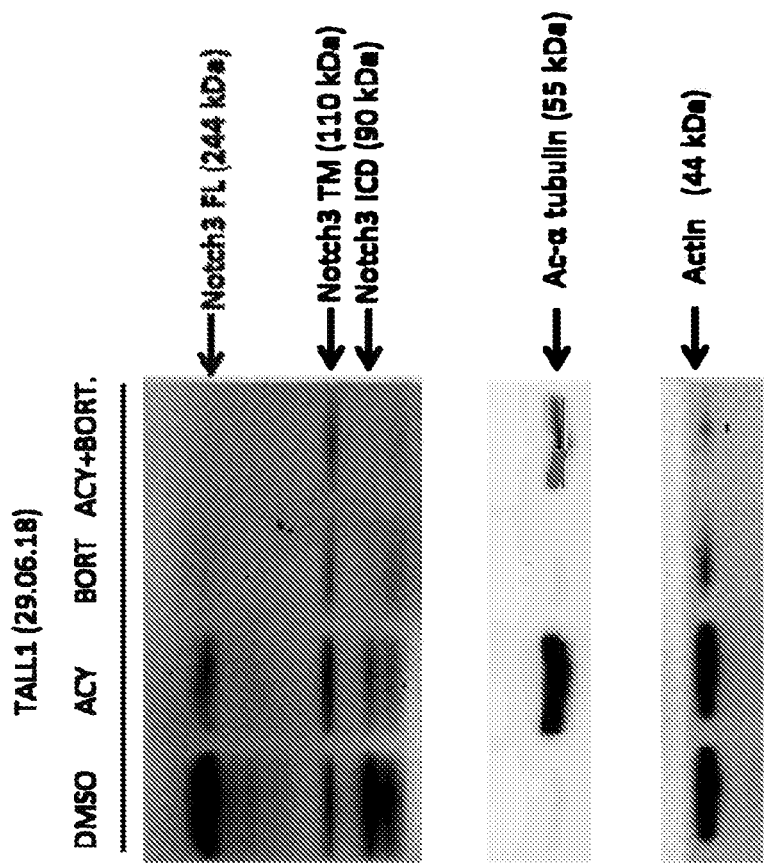
FIG. 9 shows the results of some assays carried out to verify the effects of rocilinostat and bortezomib in T-ALL cells.
Figure 9:
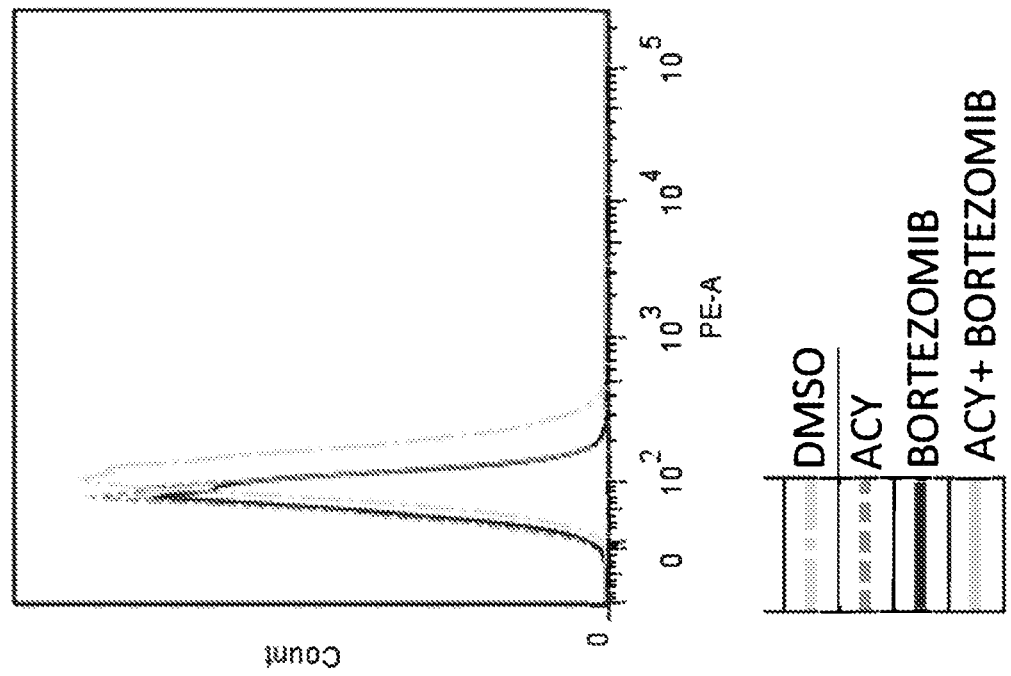

The results of FIG. 9 show that treatment with rocilinostat (8 $\mu$M) after 16 hours reduces Notch3 membrane expression in TALL1 cells. Bortezomib (20 $\mu$M) also has a negative effect on Notch3 expression but such effect is associated with high cytotoxicity, as evidenced by the marked reduction of actin in the Western blot panel on the right.

Figure 10:
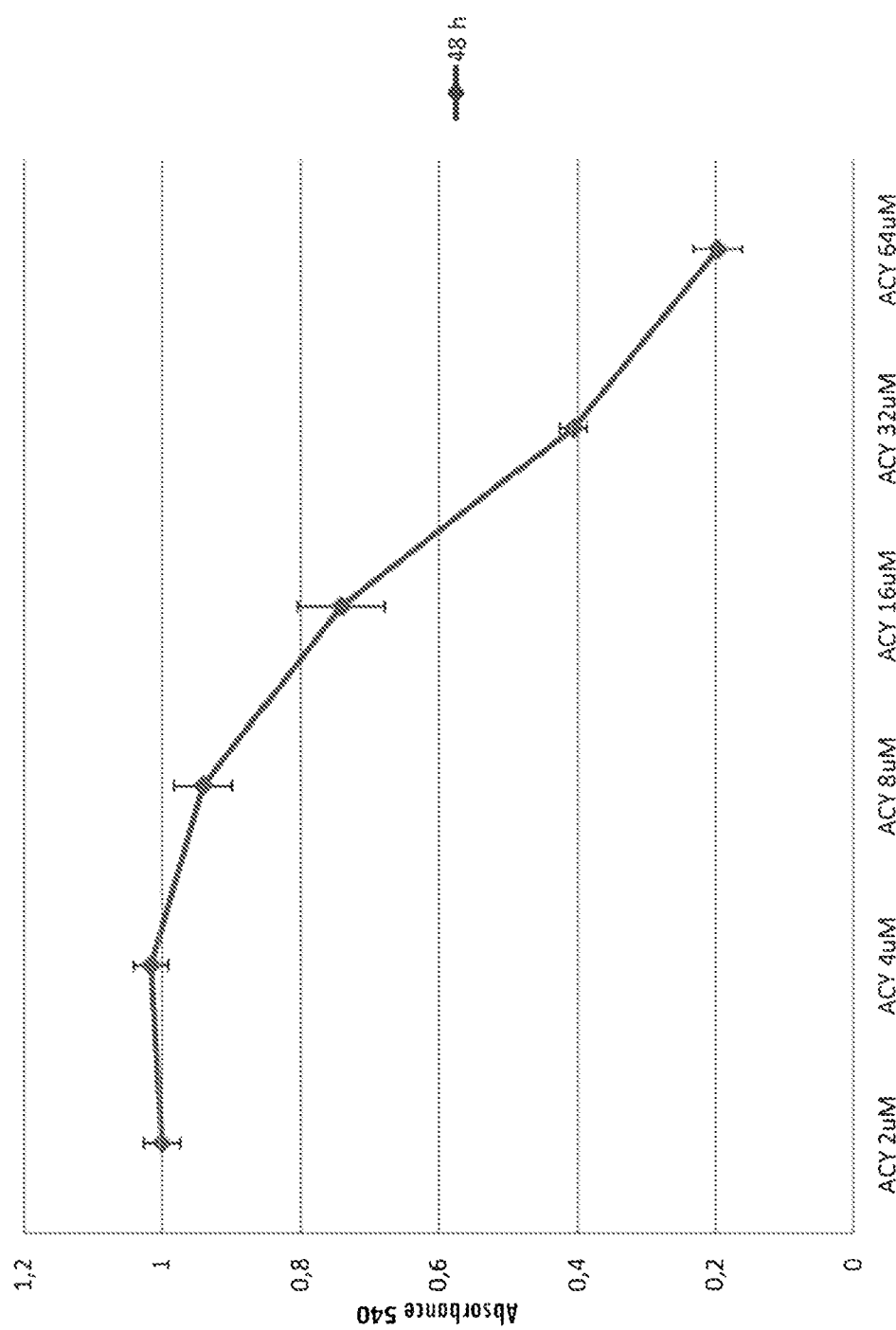
FIG. 10 shows the graph of dose-response results on the MDA-MB-468 breast cancer line.

The graph of FIG. 10 shows the results of a dose-response experiment (SRB assay) of three experiments performed (each with 5 technical replicates) in the MDA-MB-468 breast cancer line, characterized by high Notch3 expression levels.

Figure 11:
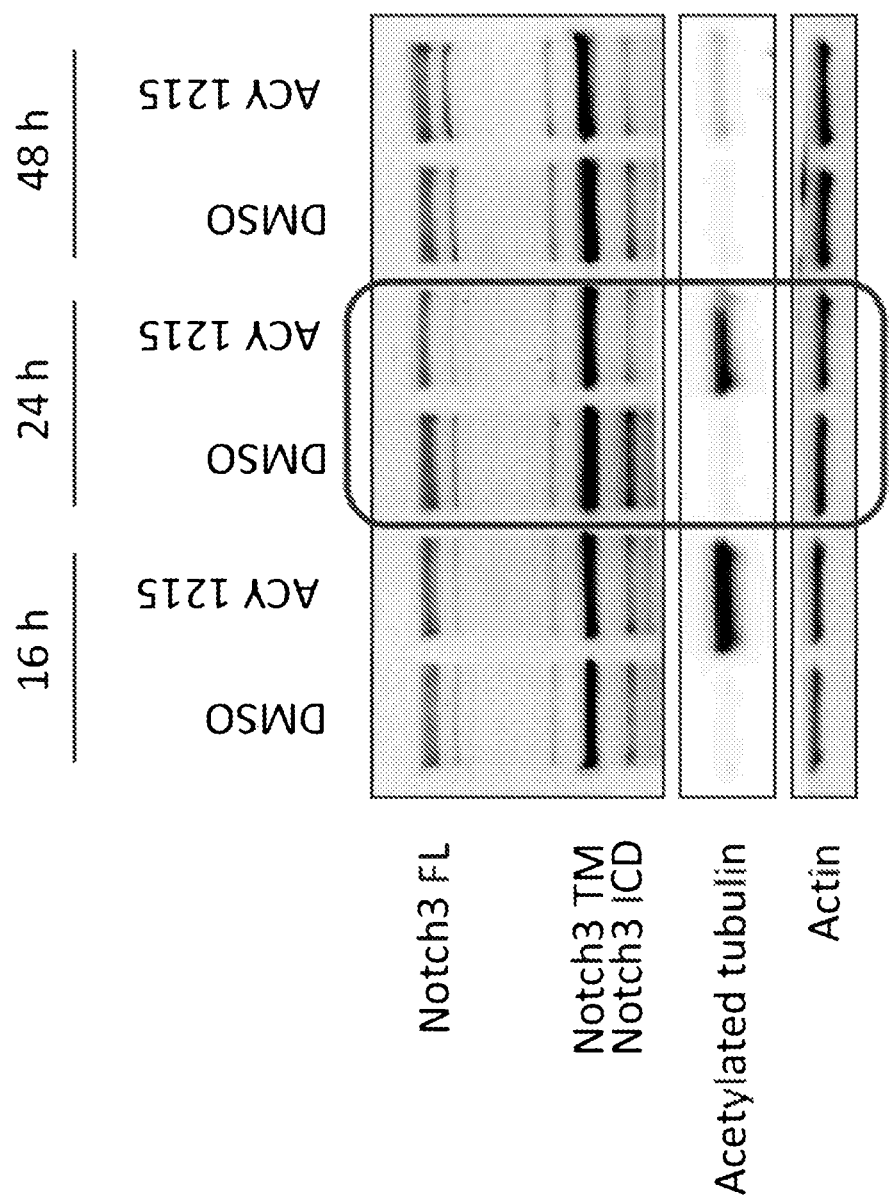
FIG. 11 shows the effects of rocilinostat on Notch3 expression in MDA-MB-468 cells.

In the assay of FIG. 11, Rocilinostat (ACY 1215) is used at a concentration of 8 $\mu$M in MDA-MB-468 cells. The expression of Notch3 and other markers was evaluated in cellular lysate by Western blotting. The results show that: at 16 hours the target (HDAC6) is inhibited but Notch3 is not reduced, at 24 hours the target is inhibited and there is a drop in Notch3—all forms, at 48 hours: the target is no longer inhibited and Notch3 levels are similar to the control (DMSO).

Figure 12:
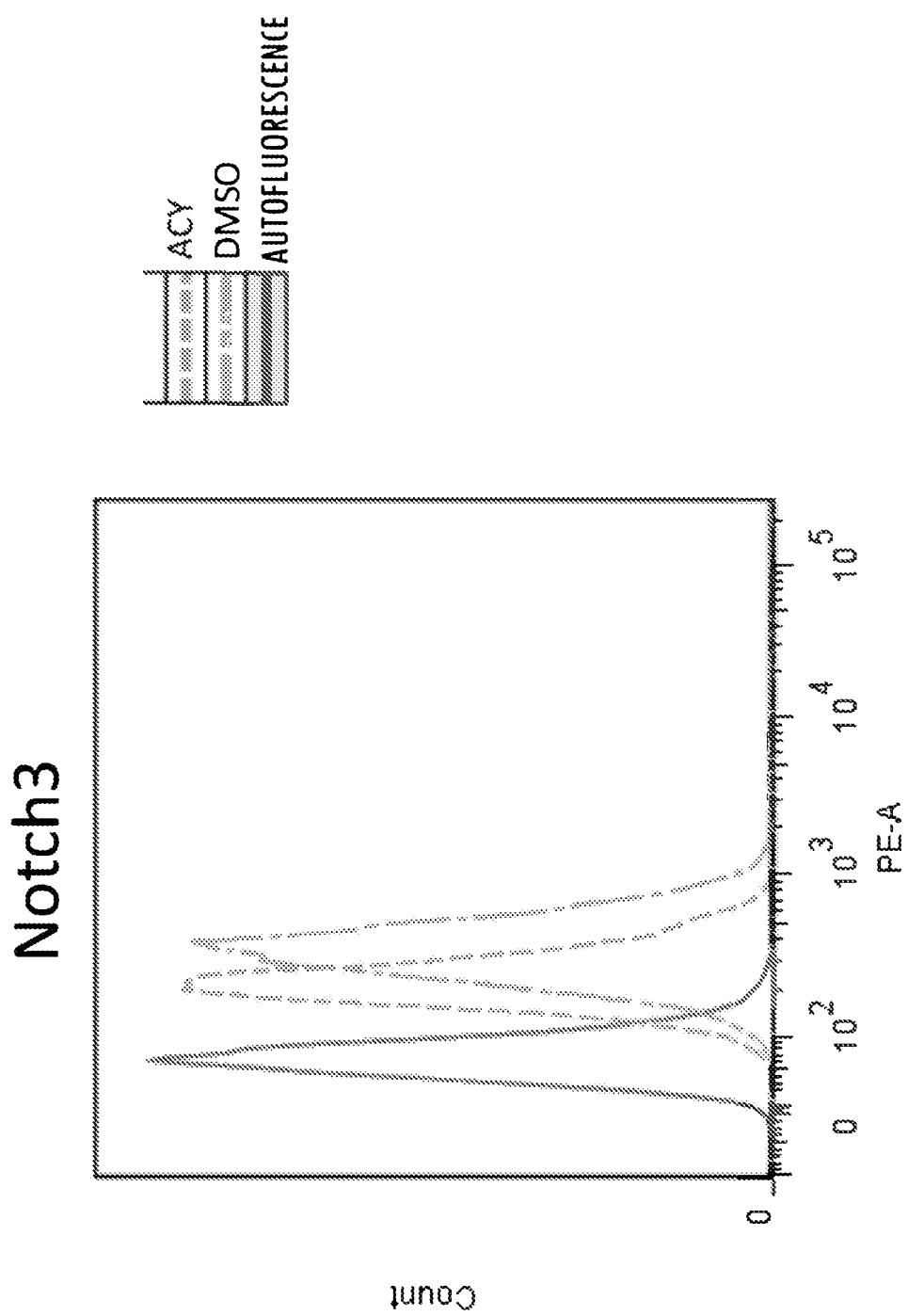
FIG. 12 shows the effects of rocilinostat on Notch3 membrane expression in MDA-MB-468 cells treated with rocilinostat.

The graph of FIG. 12 confirms the reduction of Notch3 expression in MDA-MB-468 cell membrane after treatment with rocilinostat (8 $\mu$M) at 24 hours, in accordance with the results of the WB.

Figure 13:
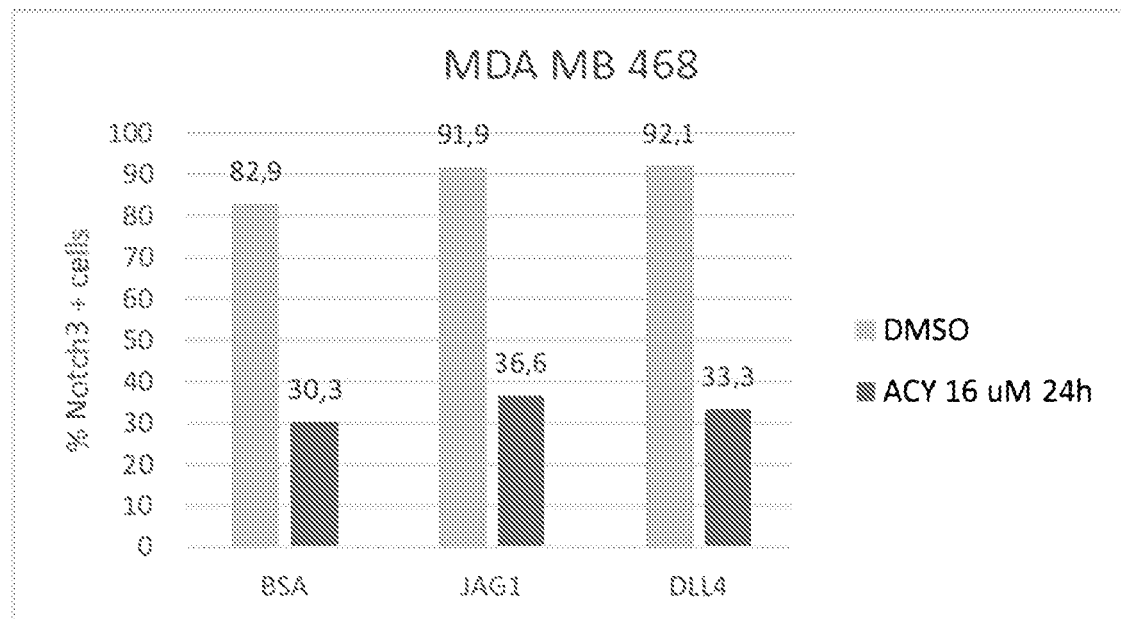
FIG. 13 shows the results of the cytofluorometric evaluation of Notch3 expression in MDA-MB-468 cells after the treatment with rocilinostat and in the presence of Notch ligands.
Figure 13:
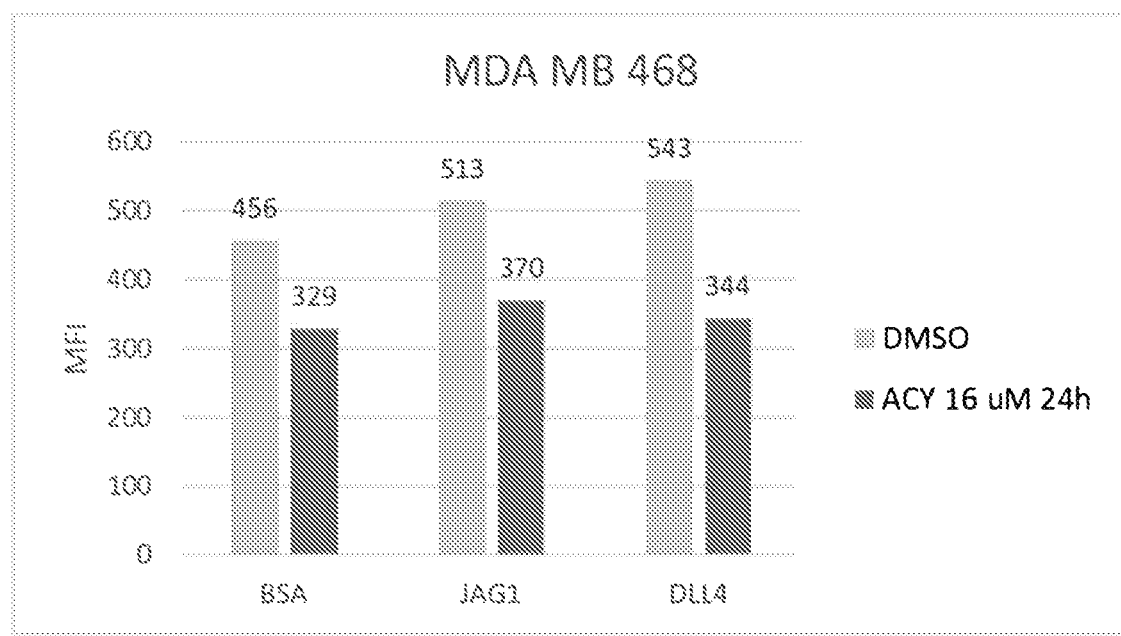

For the assay of FIG. 13, the following protocol was used:
Day 0: seeding 300,000 cells/well P6
Day 1: coating of plate with Notch ligands (ligand concentration 4 ng/uL)
Day 2: cell plating
Day 3 treatment with rocilinostat (16 $\mu$M) or control (DMSO)
Day 4: Marking+reading by cytofluorometer The results demonstrate a marked negative effect of rocilinostat on Notch3 expression both in terms of percentage of positive cells (%) and intensity of expression (MFI). Such effect is not substantially affected by Notch ligands (JAG1 and DLL4).

Figure 14:
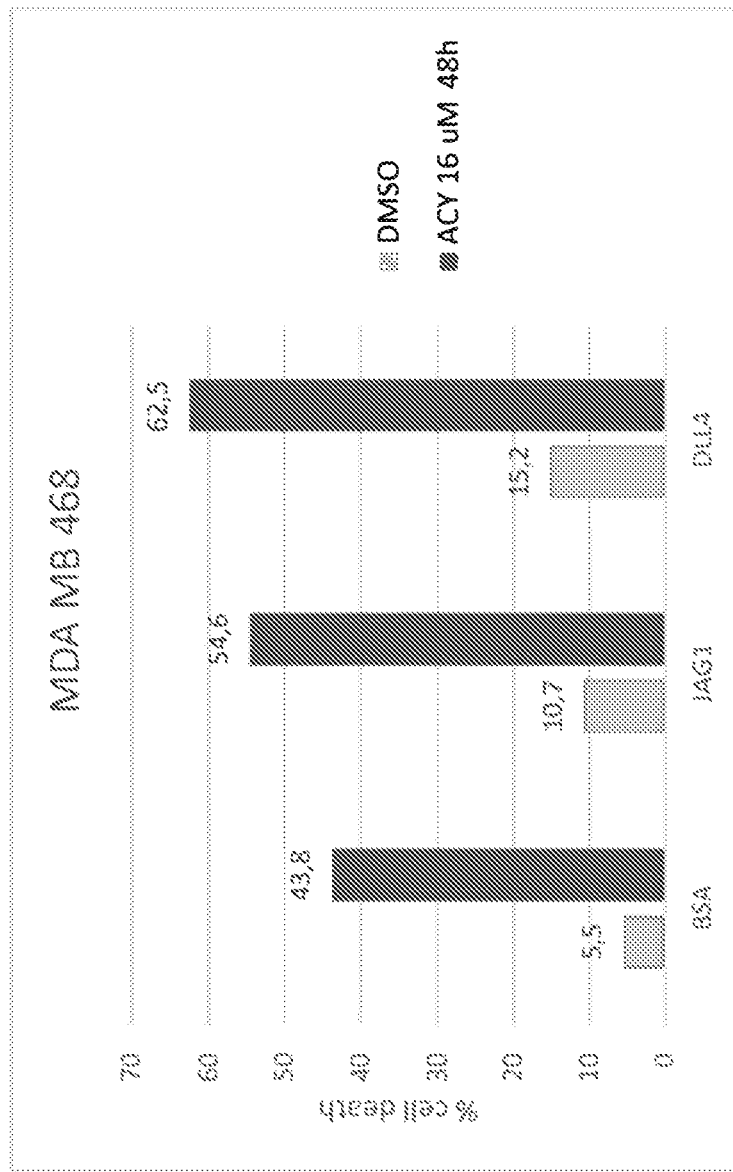
FIG. 14 shows the results of the evaluation of cell mortality induced by rocilinostat in MDA-MB-468 cells.

For the assay of FIG. 14, the following protocol was used:
Day 0: seeding 150,000 cells/well P6
Day 1: coating (ligand concentration 4 ng/uL)
Day 2: cell plating
Day 3 treatment with 16 $\mu$M rocilinostat
Day 5: marking with Annexin V/propidium iodide+reading of mortality by cytofluorometer The results show that rocilinostat (ACY) causes the death of MDA MB 468 breast cancer cells and that such effect is maintained or slightly increased in the presence of Notch ligands (JAG1 and DLL4).

Figure 15:
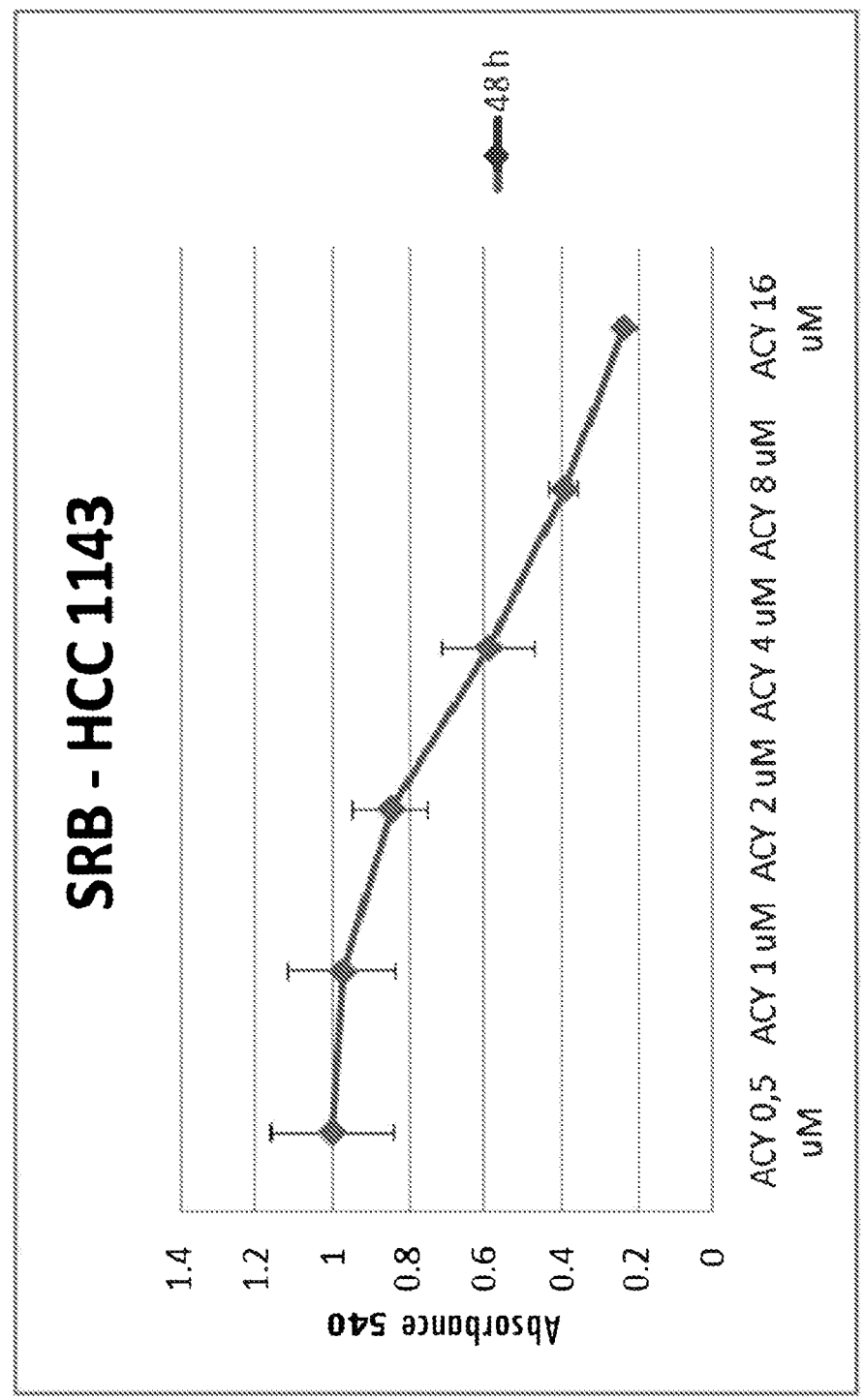
FIG. 15 shows the effects of rocilinostat (dose-response curve) in Notch3-amplified breast cancer cells (HCC-1143)

The graph in FIG. 15 shows that rocilinostat (ACY) inhibits the growth of HCC-1143 cells with dose-dependent effects.

Figure 16:
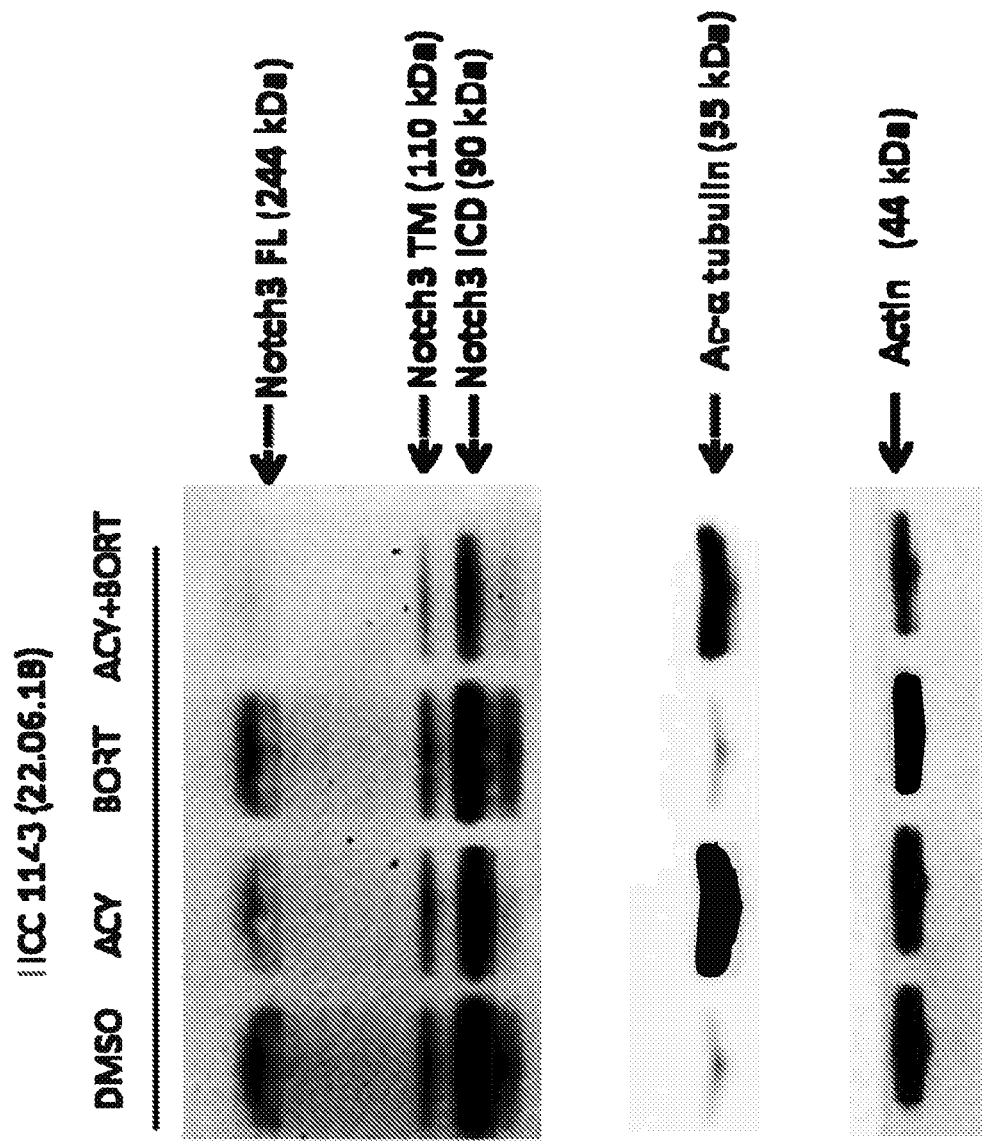
FIG. 16 shows the effects of rocilinostat on Notch3 expression in HCC-1143 cells, whereas the increase in acetylated tubulin levels confirms the activity of rocilinostat.

To evaluate the effects of rocilinostat on Notch3 expression in HCC-1143 cells, HCC-1143 cells were treated in vitro with rocilinostat at a concentration of 8 $\mu$M for 24 hours. As shown in FIG. 16, treatment with this HDAC6i decreases the levels of NOTCH3 FL protein. The increase in acetylated tubulin levels confirms the activity of rocilinostat.

The graph of FIG. 17A shows a reduction in Notch3 membrane expression after treatment with rocilinostat; the graph in FIG. 17B shows that the combined treatment rocilinostat+bortezomib causes a further reduction in Notch3 expression in HCC-1143 cells.

The following protocol was used for the graphs of FIG. 18:
Day 1: coating of plate with Notch ligands (ligand concentration 4 ng/uL)
Day 2: seeding 300,000 HCC-1143 cells/well P6
Day 3 treatment with rocilinostat (16 $\mu$M) or control (DMSO)
Day 4: marking+reading by cytofluorometer The results demonstrate a moderate negative effect of rocilinostat on Notch3 expression in terms of percentage of positive cells (%), more evident in terms of intensity of expression (MFI). Such effects are not much influenced by Notch ligands (JAG1 and DLL4).

For the graphs of FIG. 19, the following protocol was used:
Day 1: coating (ligand concentration 4 ng/uL)
Day 2: seeding 150,000 cells/well P6
Day 3 treatment with 16 $\mu$M rocilinostat
Day 5: marking with Annexin V/propidium iodide+reading of mortality by cytofluorometer.

The results show that rocilinostat (16 $\mu$M) causes the death of HCC1143 breast cancer cells and that such effect is maintained in the presence of Notch ligands (JAG1 and DLL4).

The evidence gathered and commented on above broadly supports the statements that:
- Rocilinostat has negative effects on Notch3 FL expression both on the cellular lysate and on the surface of T-ALL and solid tumor cells (breast cancer);
- rocilinostat-sensitive breast cancer lines express high Notch3 levels;
- the effects of rocilinostat may be enhanced by bortezomib; the identification of the optimal concentration requires the performance of dose-response experiments with bortezomib on each cell line under study;
- rocilinostat reduces proliferation and induces apoptosis in the tumoral lines expressing Notch3;
- the effects of rocilinostat on cell lines are maintained in the presence of Notch ligands.

The invention claimed is:

1. A method for treating neoplasia in a patient in need of such treatment, the method comprising administering to said patient a compound represented by an inhibitor of the histone deacetylase 6 (HDAC6), wherein one or more of the following conditions have been ascertained in said patient:
   NOTCH3 gene mutations or amplification,
   higher than normal expression levels of the NOTCH3 gene, and
   NOTCH1 gene mutations.

2. The method of claim 1, wherein said neoplasia is represented by T-cell acute lymphoblastic leukemia (T-ALL).

3. The method of claim 1, wherein said compound is selected from the group consisting of: ricolinostat (ACY-1215), ACY-241, and KA2507.

4. The method of claim 1, wherein said neoplasia is T-cell acute lymphoblastic leukemia (T-ALL) and the patient is an adult patient.

5. The method of claim 1, wherein said neoplasia is T-cell acute lymphoblastic leukemia (T-ALL) and the patient is a pediatric patient.

6. The method of claim 1, the method further comprising administering a compound represented by an inhibitor of the histone deacetylase 6 (HDAC6), in combination with one or more drugs selected from the group consisting of:
   proteasome inhibitors,
   steroidal anti-inflammatory drugs, and
   chemotherapeutics.

7. The method of claim 6, wherein said proteasome inhibitors is bortezomib.

8. The method of claim 6, wherein said steroidal anti-inflammatory drugs are selected from the group consisting of: dexamethasone and prednisone.

9. The method of claim 1, wherein said compound is administered in an amount of about 150-170 mg/day.

10. The method of claim 9, wherein said compound administered from day 1 to day 5 and from day 8 to day 12 of a treatment cycle.

11. The method of claim 1, wherein said compound is administered orally.

12. A method for treating neoplasia in a patient in need of such treatment, the method comprising:
   administering to said patient a compound represented by an inhibitor of the histone deacetylase 6 (HDAC6), in combination with one or more drugs selected from the group consisting of: proteasome inhibitors, steroidal anti-inflammatory drugs, and chemotherapeutics, and
   wherein one or more of the following conditions have been ascertained in said patient: NOTCH3 gene mutations or amplification, higher than normal expression levels of the NOTCH3 gene, and NOTCH1 gene mutations.

13. The method of claim 12, wherein said neoplasia is represented by T-cell acute lymphoblastic leukemia (T-ALL).

14. The method of claim 12, wherein said compound is selected from the group consisting of: ricolinostat (ACY-1215), ACY-241, and KA2507.

15. The method of claim 12, wherein said proteasome inhibitors is bortezomib.

16. The method of claim 12, wherein said steroidal anti-inflammatory drugs are selected from the group consisting of: dexamethasone and prednisone.

17. A method for treating neoplasia in a patient in need of such treatment, the method comprising:
   administering to said patient a compound represented by an inhibitor of the histone deacetylase 6 (HDAC6), in combination with one or more drugs selected from the group consisting of: proteasome inhibitors comprising bortezomib, steroidal anti-inflammatory drugs selected from the group consisting of: dexamethasone and prednisone, and chemotherapeutics, and
   wherein one or more of the following conditions have been ascertained in said patient: NOTCH3 gene mutations or amplification, higher than normal expression levels of the NOTCH3 gene, and NOTCH1 gene mutations.

18. The method of claim 17, wherein said neoplasia is represented by T-cell acute lymphoblastic leukemia (T-ALL).

19. The method of claim 17, wherein said compound is selected from the group consisting of: ricolinostat (ACY-1215), ACY-241, and KA2507.

20. The method of claim 17, wherein said compound is administered orally.

* * * * *